(12) United States Patent
Agresta

(10) Patent No.: US 10,905,692 B2
(45) Date of Patent: Feb. 2, 2021

(54) COMBINATION THERAPY FOR TREATING MALIGNANCIES

(71) Applicant: Agios Pharmaceuticals, Inc., Cambridge, MA (US)

(72) Inventor: Samuel V. Agresta, Lexington, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/768,480

(22) PCT Filed: Oct. 14, 2016

(86) PCT No.: PCT/US2016/057083
§ 371 (c)(1),
(2) Date: Apr. 13, 2018

(87) PCT Pub. No.: WO2017/066599
PCT Pub. Date: Apr. 20, 2017

(65) Prior Publication Data
US 2018/0311249 A1 Nov. 1, 2018

Related U.S. Application Data

(60) Provisional application No. 62/255,194, filed on Nov. 13, 2015, provisional application No. 62/242,256, filed on Oct. 15, 2015.

(51) Int. Cl.
| | | |
|---|---|---|
| *A61K 31/53* | (2006.01) | |
| *A61K 31/136* | (2006.01) | |
| *A61K 31/704* | (2006.01) | |
| *A61K 31/7048* | (2006.01) | |
| *A61K 31/7068* | (2006.01) | |
| *A61P 35/02* | (2006.01) | |

(52) U.S. Cl.
CPC ............ *A61K 31/53* (2013.01); *A61K 31/136* (2013.01); *A61K 31/704* (2013.01); *A61K 31/7048* (2013.01); *A61K 31/7068* (2013.01); *A61P 35/02* (2018.01); *A61K 2300/00* (2013.01)

(58) Field of Classification Search
CPC .... A61K 31/53; A61K 31/136; A61K 31/704; A61K 31/7048; A61K 31/7068; A61K 2300/00; A61P 35/02
See application file for complete search history.

(56) References Cited

U.S. PATENT DOCUMENTS

| | | |
|---|---|---|
| 9,512,107 B2 | 12/2016 | Cianchetta et al. |
| 9,656,999 B2 | 5/2017 | Cianchetta et al. |
| 9,694,013 B2 | 7/2017 | Agresta et al. |
| 9,724,350 B2 | 8/2017 | Travins et al. |
| 9,732,062 B2 | 8/2017 | Cianchetta et al. |
| 9,738,625 B2 | 8/2017 | Agresta et al. |
| 9,751,863 B2 | 9/2017 | Zhang |
| 2002/0051820 A1 | 5/2002 | Shell et al. |
| 2003/0039688 A1 | 2/2003 | Shell et al. |
| 2003/0104053 A1 | 6/2003 | Gusler et al. |
| 2003/0104062 A1 | 6/2003 | Berner et al. |
| 2012/0121515 A1 | 5/2012 | Dang et al. |
| 2013/0316385 A1 | 11/2013 | Cantley et al. |
| 2017/0298045 A1 | 7/2017 | Cianchetta et al. |
| 2017/0157132 A1 | 10/2017 | Wu et al. |
| 2017/0246174 A1 | 10/2017 | Amatangelo et al. |
| 2017/0266193 A1 | 10/2017 | Agresta |
| 2017/0305885 A1 | 10/2017 | Agresta |

FOREIGN PATENT DOCUMENTS

| | | |
|---|---|---|
| WO | WO 2015/006592 A1 | 1/2015 |
| WO | WO 2015/017821 A2 | 2/2015 |
| WO | WO 2015/018060 A1 | 2/2015 |
| WO | WO 2016/126798 A1 | 8/2016 |
| WO | WO 2017/066611 A1 | 4/2017 |

OTHER PUBLICATIONS

Ellwood-Yen et al., Proceedings of the 105th Annual Meeting of the American Association for Cancer Research; Apr. 5-9, 2014; San Diego, CA, abstract. (Year: 2014).*
Van der Jagt et al., Blood, 2005, 106:4619. (Year: 2005).*
Entry for Enasidenib, PubChem website, https://pubchem.ncbi.nlm.nih.gov/compound/89683805, accessed online on Sep. 10, 2019. (Year: 2019).*
Aghili et al., "Hydroxyglutaric aciduria and malignant brain tumor: a case report and literature review," *J Neurooncol.*, 91:233-236 (2009).
Anonymous, "NCT02632708, ClinicalTrials.gov archive, updated on Dec. 16, 2015," ClinicalTrials.gov, Retrieved from the internet: URL:https://clinicaltrials.gov/archive/NCT02632708/2015_12_15, retrieved on Jan. 12, 2017, 6 pages.
Berge et al., "Pharmaceutical salts," *J. Pharm. Sci.*, 66(1):1-19 (1977).
Cheson et al., "Clinical application and proposal for modification of the International Working Group (IWG) response criteria in myelodysplasia," *Blood*, 108(2):419-425 (2006).
Cheson et al., "Revised recommendations of the International Working Group for Diagnosis, Standardization of Response Criteria, Treatment Outcomes, and Reporting Standards for Therapeutic Trials in Acute Myeloid Leukemia," *J. Clin. Oncol.*, 21(24):4642-4649 (2003).
Dang et al., "Cancer-associated IDH1 mutations produce 2-hydroxyglutarate," *Nature* 462:739-744 (2009).
Foundation Medicine, FoundationOne® Heme,Technical Information and Test Overview, Retrieved on Apr. 6, 2017. Retrieved from the internet: URL: http://foundationone.com/learn.php.

(Continued)

*Primary Examiner* — Jonathan S Lau
(74) *Attorney, Agent, or Firm* — Jones Day

(57) ABSTRACT

Provided are methods and compositions for treating AML in patients carrying an IDH2 mutation using a combination of an inhibitor of a mutant IDH2 enzyme and an AML induction and consolidation therapy.

22 Claims, 6 Drawing Sheets

(56) References Cited

OTHER PUBLICATIONS

Geisbrecht et al., "The human PICD gene encodes a cytoplasmic and peroxisomal NADP(+)—dependent isocitrate dehydrogenase," *J. Biol. Chem.*, 274(43):30527-30533 (1999).
Genbank Accession No. NM_002168.2 (Feb. 22, 2014).
Genbank Accession No. NM_005896.2 (Sep. 2, 2013).
Genbank Accession No. NP_002159.2 (Apr. 30, 2016).
Genbank Accession No. NP_005887.2 (Jan. 4, 2017).
Gerhard et al., "The status, quality, and expansion of the NIH full-length cDNA project: the Mammalian Gene Collection (MGC)," *Genome Res.*, 14(10B):2121-2127 (2004).
IDHIFA label issued Aug. 2017, available at https://www.accessdata.fda.gov/drugsatfda_docs/label/2017/209606s0001b1.pdf.
Kölker et al., "NMDA receptor activation and respiratory chain complex V inhibition contribute to neurogeneration in D-2-hydroxyglutaric aciduria," *Eur. J Neurosci.*, 16:21-28 (2002).
Kölker et al., "White matter disease in cerebral organic acid disorders: clinical implications and suggested pathomechanisms," *Neuropediatrics*, 33:225-231 (2002).
Latini et al., "D-2-hydroxyglutaric acid induces oxidaitive stress in cerebral cortex of young rats," *Eur. J Neurosci.*, 17:2017-2022 (2003).
Luo et al., "Simultaneous determination of multiple intracellular metabolites in glycolysis, pentose phosphate pathway and tricarboxylic acid cycle by liquid chromatography-mass spectrometry," *J. Chromatogr* A., 1147:153 164(2007).
Miyawaki et al. "Long-term follow-up of the randomized JALSG AML 201 study comparing high dose Ara-C therapy with conventional consolidation therapy in adult acute myeloid leukemia (AML)," *Blood*, 112:135 (2008).
Munger et al., "Systems-level metabolic flux profiling identifies fatty acid synthesis as a target for antiviral therapy," *Nat. Biotechnol.*, 26(10):1179-1186 (2008).
Oken et al., "Toxicity and response criteria of the Eastern Cooperative Oncology Group," *Am. J. Clin. Oncol.*, 5(6):649-655 (1982).
Ravandi et al., "Prognostic significance of alterations in IDH enzyme isoforms in patients with AML treated with high-dose cytarabine and idarubicin," *Cancer*, 118(10):2665-2673 (2011).
Stein et al., "Abstract CT103: Clinical safety and activity in a phase I trial of AG-221, a first in class, potent inhibitor of the IDH2-mutant protein, in patients with IDH2 mutant positive advanced hematologic malignancies," in Proceedings: AACR Annual Meeting, Apr. 5-9, 2014, San Diego, CA, *Cancer Research*, Oct. 1, 2014, retrieved from the internet: URL:http://cancerres.aacrjournals.org/content/74/19_Supplement/CT103, retrieved on Jan. 12, 2017, 5 pages.
Stein, "AG-221 sparks durable remissions in IDH2-mutated AML," *Oncology Report*, Dec. 7, 2014, Retrieved from the Internet: URL:http://www.targetendonc.com/conference/ash-2014/ag-221-sparks-durable-remissions-in-idh2-mutated-aml, retrieved on Jan. 12, 2017, 3 pages.
Struys et al., "Mutations in the D-2-Hydroxyglutarate dehydrogenase gene cause D-2-hydroxyglutaric aciduria," *Am. J. Hum. Genet.*, 76:358-360 (2005).
Wajner et al., "The role of oxidative damage in the neuropathology of organic acidurias: insights from animal studies," *J. Inherit. Metab. Dis.*, 27:427-448 (2004).
Stein et al., "Ivosidenib or enasidenib combined with standard induction and consolidation chemotherapy in patients with newly diagnosed AML with an IDH1 or IDH2 mutation is safe, effective and leads to MRD-negative complete remissions," presented at the 60th American Society of Hematology (ASH) Annual Meeting, Dec. 1-4, 2018, San Diego, CA, 21 pages.
Goodman and Gilman, The Pharmacological Basis of Therapeutics, 2001, 10th ed., p. 54-56.
Morris, Cancer: A comprehensive Clinical Guide, 1998, p. 49-59.
Van Der Jagt, Leukemia and Lymphoma, 2006, vol. 47, No. 4, pp. 697-706.

* cited by examiner

COMBINATION THERAPY FOR TREATING MALIGNANCIES

CROSS REFERENCE TO RELATED APPLICATIONS

This application is a U.S. National Stage filing under 35 U.S.C. § 371 of International Application No. PCT/US2016/057083, filed Oct. 14, 2016, which claims the benefit of the priority to U.S. Provisional Application Nos. 62/242,256, filed Oct. 15, 2015, and 62/255,194, filed Nov. 13, 2015, the disclosure of each of which is incorporated herein by reference in its entirety.

FIELD

Provided herein are combination therapies for treating hematological malignancies. In one embodiment, the hematological malignancy is acute myeloid leukemia (AML). In one embodiment, the therapies involve treatment with an IDH2 inhibitor and an AML induction and consolidation therapy.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM 002168.2 and NP 002159.2 respectively. The nucleotide and amino acid sequence for human IDH2 are also described in, e.g., Huh et al., Submitted (November 1992) to the EMBL/GenBank/DDBJ databases; and The MGC Project Team, Genome Res. 14:2121-2127 (2004).

Non-mutant, e.g., wild type, IDH2 catalyzes the oxidative decarboxylation of isocitrate to α-ketoglutarate (α-KG) thereby reducing NAD$^+$ (NADP$^+$) to NADH (NADPH), e.g., in the forward reaction:

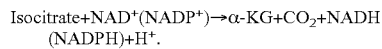
Isocitrate+NAD$^+$(NADP$^+$)→α-KG+CO$_2$+NADH (NADPH)+H$^+$.

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L. et al., Nature 462:739-44, 2009).

Somatic IDH2 mutations occur in a spectrum of solid and hematologic tumors and premalignant disorders, including acute myeloid leukemia (AML) and myelodysplastic syndrome (MDS). Around 15% of AML patient population contains the IDH2 gene mutation which leads to production of oncometabolite 2HG, the accumulation of 2HG inhibits the ten-eleven translocation (TET) group of DNA demethylases resulting in a DNA hypermethylation phenotype. The increased DNA methylation leads to differentiation block and propogation of AML (Wang et al., Science 340:622-626, 2013).

The development of selective inhibitors of IDH2 mutant enzyme has provided the possibility of therapeutic benefit to AML patients carrying the IDH2 mutation. There have been successful responses in the clinic with decreased blast population and benefit of differentiated functional blood cells. However, the genetic load is present in the patients even with good overall response. Therefore, there is a need for improved therapies for treating AML having IDH2 mutations.

SUMMARY

In one embodiment, provided herein are methods of treating acute myeloid leukemia (AML), characterized by the presence of a mutant allele of IDH2, by administering to a subject a therapeutically effective amount of a combination of a mutant IDH2 inhibitor and an AML induction and consolidation therapy.

In one embodiment, the mutant IDH2 inhibitor is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, or a pharmaceutically acceptable salt, solvate, tautomer, stereoisomer, isotopologue, prodrug, metabolite, or a polymorph thereof (COMPOUND 1).

In one embodiment, the AML, characterized by the presence of a mutant allele of IDH2, is refractory, or relapsed AML.

In one embodiment, the AML induction therapy is a combination of Cytarabine and Daunorubicin. In one embodiment, the AML induction therapy is a combination of Cytarabine and Idarubicin.

In one embodiment, the AML consolidation therapy is Cytarabine. In one embodiment, the AML consolidation therapy is a combination of Mitoxantrone and Etoposide.

In one embodiment, provided herein is a method of treating AML characterized by the presence of a mutant allele of IDH2, comprising administering to a subject a therapeutically effective amount of COMPOUND 1 and the AML induction therapy and consolidation therapy.

In one embodiment, provided herein is a method of treating AML characterized by the presence of a mutant allele of IDH2, comprising administering to a subject a pharmaceutical composition comprising a therapeutically effective amount of COMPOUND 1 and the AML induction therapy and consolidation therapy.

In one embodiment, provided herein is a method of treating AML, wherein AML is selected from newly diagnosed AML, untreated AML, AML arising from myelodysplastic syndrome (MDS), AML arising from antecedent hematologic disorder (AHD) and AML arising after exposure to genotoxic injury. In certain embodiments, the genotoxic injury results from radiation and/or chemotherapy. In one embodiment, provided herein is a method of treating AML arising after exposure to genotoxic injury resulting from radiation and/or chemotherapy.

DETAILED DESCRIPTION

Figure 1:
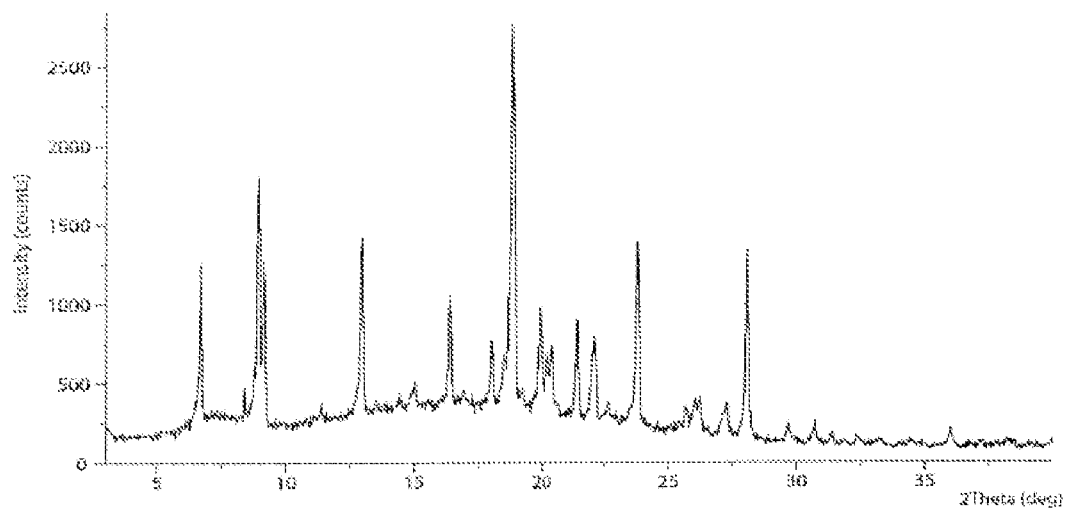
FIG. 1 is an X-ray powder diffractogram (XPRD) of COMPOUND 1 form 1.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH2 inhibitor" or "inhibitor of IDH2 mutant(s)" means a molecule e.g., a polypeptide, peptide, or small molecule (e.g., a molecule of less than 1,000 daltons), or aptomer, that binds to an IDH2 mutant subunit and inhibits neoactivity, e.g., by inhibiting formation of a dimer, e.g., a homodimer of mutant IDH2 subunits or a heterodimer of a mutant and a wildype subunit. In some embodiments, the neoactivity inhibition is at least about 60%, 70%, 80%, 90%, 95% or 99% as compared to the activity in the absence of the mutant IDH2 inhibitor. In one embodiment, the mutant IDH2 inhibitor is COMPOUND 1.

The term "elevated levels of 2HG" means 10%, 20% 30%, 50%, 75%, 100%, 200%, 500% or more 2HG is present in a subject that carries a mutant IDH2 allele than is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2), lessen the severity of the disease/disorder or improve the symptoms associated with the disease/disorder. In one embodiment, the disease or disorder is acute myelogenous leukemia (AML) characterized by the presence of a mutant allele of IDH2. In one embodiment, the disease or disorder is myelodysplastic syndrome (MDS) characterized by the presence of a mutant allele of IDH2. In one embodiment, the disease or disorder is chronic myelomonocytic leukemia (CMML) characterized by the presence of a mutant allele of IDH2. In one embodiment, the disease or disorder is myeloid sarcoma characterized by the presence of a mutant allele of IDH2. In one embodiment, the disease or disorder is multiple myeloma characterized by the presence of a mutant allele of IDH2. In one embodiment, the disease or disorder is lymphoma (e.g., T-cell lymphoma), characterized by the presence of a mutant allele of IDH2).

An amount of a compound, including a pharmaceutically acceptable salt, solvate, tautomer, stereoisomer, isotopologue, prodrug, metabolite, or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, metabolite, or a polymorph thereof, which is effective, upon single or multiple dose administration to a subject, in treating a cell, or in curing, alleviating, relieving or improving a subject with a disorder beyond that expected in the absence of such treatment.

Leukemia, in particular AML, response to treatment can be assessed based on the International Working Group Response Criteria in AML (Cheson et al. Revised recommendations of the International Working Group for diagnosis, standardization of response criteria, treatment outcomes, and reporting standards for therapeutic trials in acute myeloid leukemia. *J Clin Oncol* 2003; 21(24):4642-9).

| Response Criterion | Time of Assessment | Neutrophils (µL) | Platelets (µL) | Bone Marrow Blasts (%) | Other |
|---|---|---|---|---|---|
| Early Treatment assessment | 7-10 days after therapy | NA | NA | <5 | |
| Morphologic Leukemia-free State | Varies by protocol | NA | NA | <5 | Flow cytometry EMD |

-continued

| Response Criterion | Time of Assessment | Neutrophils (µL) | Platelets (µL) | Bone Marrow Blasts (%) | Other |
|---|---|---|---|---|---|
| Morphologic CR | Varies by protocol | ≥1,000 | ≥100,000 | <5 | Transfusion EMD |
| Cytogenetic CR (CRc) | Varies by protocol | ≥1,000 | ≥100,000 | <5 | Cytogenetics - normal, EMD |
| Molecular CR (CRm) | Varies by protocol | ≥1,000 | ≥100,000 | <5 | Molecular - negative, EMD |
| Morphologic CR with incomplete blood recovery (CRi) | Varies by protocol | Fulfill all criteria for CR except for residual neutropenia (<1,000/µL) or thrombocytopenia (<100,000/µL). | | | |
| Partial Remission | Varies by protocol | ≥1,000 | ≥100,000 | Decrease ≥50 resulting in 5 to 25 | Blasts ≤5% if Auer rod positive |
| Relapse after CR | Varies by protocol | Reappearance of leukemic blasts in the peripheral blood or ≥5% blasts in the bone marrow not attributable to any other cause (eg, bone marrow regeneration after consolidation therapy). | | | |

Key:
AML = acute myelogenous leukemia;
CR = complete remission;
EMD = extramedullary disease;
IWG = International Working Group;
NA = not applicable.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 1 may be produced as one or more single crystalline forms of COMPOUND 1. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 1 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a COMPOUND 1 that is at least 70% crystalline. In other embodiments, substantially crystalline refers to a COMPOUND 1 that is at least 90% crystalline.

The term "isolated" refers to forms that may be at least a particular weight percent of a particular crystalline form of compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci. Vol.* 66, pp. 1-19.

The term "acute myeloid leukemia (AML)", as used herein, refers to cancer of the myeloid line of blood cells, characterized by the rapid growth of abnormal white blood cells that accumulate in the bone marrow and interfere with the production of normal blood cells. In one embodiment, the AML is selected from newly diagnosed AML, untreated AML, AML arising from myelodysplastic syndrome (MDS), AML arising from antecedent hematologic disorder (AHD) and AML arising after exposure to genotoxic injury.

The term "refractory AML" as used herein, refers to an AML in which the high level of white blood cells does not decrease in response to a treatment.

The term "relapsed AML" as used herein, refers to an AML which does not respond to a treatment.

The term "AML induction therapy", as used herein, refers to a therapy given with the goal to rapidly restoring normal bone marrow function, i.e., to induce remission.

The term "AML consolidation therapy", as used herein, refers to a therapy given to maintain remission achieved as a result of the induction therapy.

The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compounds

In one embodiment, COMPOUND 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate, tautomer, stereoisomer, isotopologue, prodrug, metabolite, or a polymorph thereof, having the following formula:

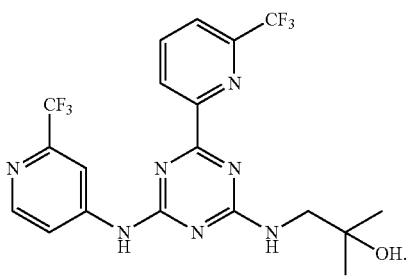 [SMILES: CC(C)(O)CNc1nc(Nc2ccnc(C(F)(F)F)c2)nc(-c2cccc(C(F)(F)F)n2)n1]

COMPOUND 1 may also comprise one or more isotopic substitutions ("isotopologues"). For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. For example, COMPOUND 1 is enriched in a specific isotopic form of H, C and/or O by at least about 60%, 65%, 70%, 75%, 80%, 85%, 90%, 95%, 96%, 97%, 98%, or 99%.

COMPOUND 1 in certain embodiments may also be represented in multiple tautomeric forms, in such instances, one aspect of the invention expressly includes all tautomeric forms of COMPOUND 1 described herein, even though only a single tautomeric form may be represented (e.g., keto-enol tautomers). All such isomeric forms of COMPOUND 1 are expressly included herein. Synthesis of COMPOUND 1 is described in US published application US-2013-0190287-A1 published Jul. 25, 2013, which is incorporated by reference in its entirety.

It may be convenient or desirable to prepare, purify, and/or handle a corresponding salt of COMPOUND 1, for example, a pharmaceutically-acceptable salt. Examples of pharmaceutically acceptable salts are discussed in Berge et al., 1977, "Pharmaceutically Acceptable Salts." *J. Pharm. Sci. Vol.* 66, pp. 1-19.

For example, if COMPOUND 1 is anionic, or has a functional group which may be anionic (e.g., —NH— may be —N—$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4{}^+$.

If COMPOUND 1 is cationic, or has a functional group that may be cationic (e.g., —NHR may be —NH$_2$R$^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. In one embodiment, COMPOUND 1 comprises the mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. Examples of suitable polymeric organic anions include, but are not limited to, those derived from the following polymeric acids: tannic acid, carboxymethyl cellulose.

COMPOUND 1 for use in the methods and pharmaceutical compositions provided herein therefore includes the COMPOUND 1 itself, as well as its pharmaceutically acceptable salts, solvates, tautomers, stereoisomers, isotopologues, prodrugs, metabolites, or polymorphs. Metabolites of COMPOUND 1 are disclosed in patent application publication WO2015/006592, which is incorporated herein by reference in its entirety. COMPOUND 1 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 1 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 1. In certain embodiments, the present disclosure provides compositions comprising COMPOUND 1 in a form described herein. In some embodiments of provided compositions, COMPOUND 1 is present as a mixture of one or more solid forms; in some embodiments of provided compositions, COMPOUND 1 is present in a single form.

In one embodiment, COMPOUND 1 is a single crystalline form, or any one of the single crystalline forms described herein. Synthesis of crystalline forms of COMPOUND 1 is described in the international application publication WO 2015/017821 published Feb. 5, 2015 and the U.S. provisional application Ser. No. 61/112,127, filed Feb. 4, 2015, both incorporated herein by reference in their entireties. Also provided are pharmaceutical compositions comprising at least one pharmaceutically acceptable carrier or diluent; and COMPOUND 1, wherein COMPOUND 1 is a single crystalline form, or any one of the crystalline forms being described herein. Also provided are uses of COMPOUND 1, wherein COMPOUND 1 is a single crystalline form, or any one of the single crystalline forms described herein, to prepare a pharmaceutical composition.

Provided herein is an assortment of characterizing information to describe the crystalline forms of COMPOUND 1. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 1 is crystalline, the remainder of COMPOUND 1 is the amorphous form of COMPOUND 1. Non-limiting examples of crystalline COMPOUND 1 include a single crystalline form of compound 1 or a mixture of different single crystalline forms. In some embodiments, COMPOUND 1 is at least 75% by weight crystalline. In some embodiments, COMPOUND 1 is at least 80% by weight crystalline. In some embodiments, COMPOUND 1 is at least 83% by weight crystalline. In some embodiments, COMPOUND 1 is at least 85% by weight crystalline. In some embodiments, COMPOUND 1 is at least 87% by weight crystalline. In some embodiments, COMPOUND 1 is at least 90% by weight crystalline. In some embodiments, COMPOUND 1 is at least 93% by weight crystalline. In some other embodiments, COMPOUND 1 is at least 95% by weight crystalline. In some embodiments, COMPOUND 1 is at least 97% by weight crystalline. In some embodiments, COMPOUND 1 is at least 99% by weight crystalline.

In another embodiment, a particular percentage by weight of the crystalline COMPOUND 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, COMPOUND 1 is at least 75% by weight crystalline. In some embodiments, COMPOUND 1 is at least 80% by weight crystalline. In some embodiments, COMPOUND 1 is at least 83% by weight of a single crystalline form. In some embodiments, COMPOUND 1 is at least 85% by weight of a single crystalline form. In some embodiments, COMPOUND 1 is at least 87% by weight of a single crystalline form. In some embodiments, COMPOUND 1 is at least 90% by weight of a single crystalline form. In some embodiments, COMPOUND 1 is at least 93% by weight of a single crystalline form. In some other embodiments, COMPOUND 1 is at least 95% by weight of a single crystalline form. In some embodiments, COMPOUND 1 is at least 97% by weight of a single crystalline form. In some embodiments, COMPOUND 1 is at least 99% by weight of a single crystalline form.

In the following description of COMPOUND 1, embodiments of the invention may be described with reference to a particular crystalline form of COMPOUND 1, as characterized by one or more properties as discussed herein. The descriptions characterizing the crystalline forms may also be used to describe the mixture of different crystalline forms that may be present in a crystalline COMPOUND 1. However, the particular crystalline forms of COMPOUND 1 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 6 may vary by ±0.2° depending upon the instrument used to obtain the data. The intensity of the XRPD peaks described in Tables 1 to 6 may vary by 10%.

Form 1

In one embodiment, a single crystalline form, Form 1, of COMPOUND 1 is characterized by the X-ray powder diffraction (XRPD) pattern shown in FIG. 1, and data shown in Table 1 obtained using CuKα radiation. In a particular embodiment, the polymorph can be characterized by one or more of the peaks taken from FIG. 1, as shown in Table 1. For example, the polymorph can be characterized by one or two or three or four or five or six or seven or eight or nine of the peaks shown in Table 1.

TABLE 1

| Angle 2- | Intensity % |
|---|---|
| 6.7 | 42.2 |
| 8.9 | 61.8 |
| 9.1 | 41.9 |
| 13.0 | 46.7 |
| 16.4 | 33.2 |
| 18.9 | 100.0 |
| 21.4 | 27.3 |
| 23.8 | 49.2 |
| 28.1 | 47.5 |

In another embodiment, Form 1 can be characterized by the peaks identified at 2θ angles of 8.9, 13.0, 18.9, 23.8, and 28.1°. In another embodiment, Form 1 can be characterized by the peaks identified at 2θ angles of 8.9, 18.9, and 23.8°.

Form 2

Figure 2:
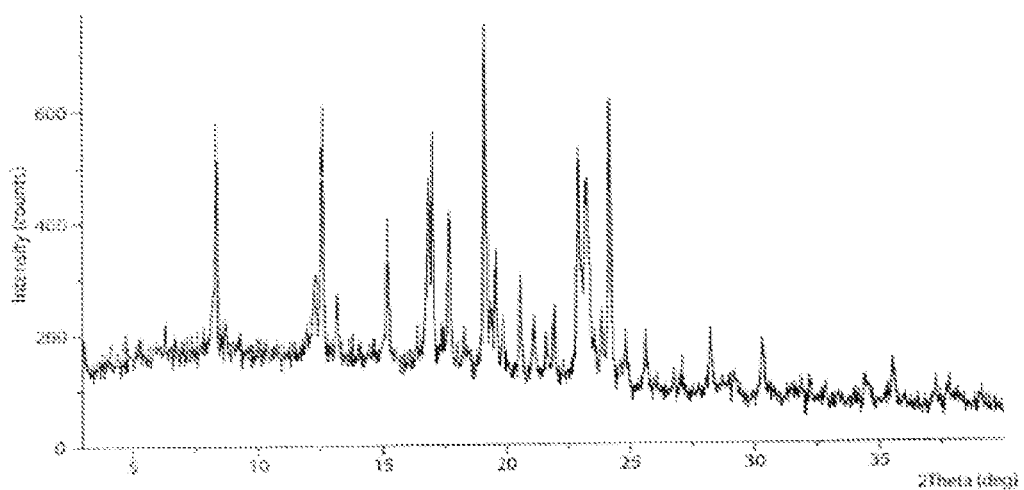
FIG. 2 is an X-ray powder diffractogram (XPRD) of COMPOUND 1 form 2.

In one embodiment, a single crystalline form, Form 2, of COMPOUND 1 is characterized by the X-ray powder diffraction (XRPD) pattern shown in FIG. 2, and data shown in Table 2, obtained using CuKα radiation. In a particular embodiment, the polymorph can be characterized by one or more of the peaks taken from FIG. 2, as shown in Table 2. For example, the polymorph can be characterized by one or two or three or four or five or six or seven or eight or nine of the peaks shown in Table 2.

TABLE 2

| Angle 2- | Intensity % |
|---|---|
| 8.4 | 65.2 |
| 12.7 | 75.5 |
| 16.9 | 57.9 |
| 17.1 | 69.4 |
| 17.7 | 48.6 |
| 19.2 | 100.0 |
| 23.0 | 69.7 |
| 23.3 | 61.1 |
| 24.2 | 87.3 |

In another embodiment, Form 2 can be characterized by the peaks identified at 2θ angles of 12.7, 17.1, 19.2, 23.0, and 24.2°. In another embodiment, Form 2 can be characterized by the peaks identified at 2θ angles of 12.7, 19.2, and 24.2°.

Form 3

Figure 3:
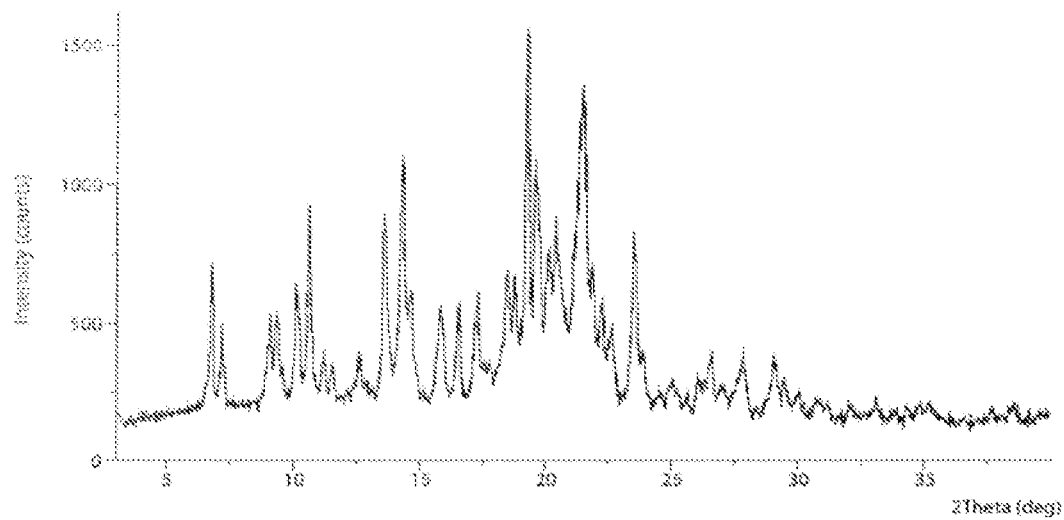
FIG. 3 is an X-ray powder diffractogram (XPRD) of COMPOUND 1 form 3.

In one embodiment, a single crystalline form, Form 3, of COMPOUND 1 is characterized by the X-ray powder diffraction (XRPD) pattern shown in FIG. 3, and data shown in Table 3, obtained using CuKα radiation. In a particular embodiment, the polymorph can be characterized by one or more of the peaks taken from FIG. 3, as shown in Table 3. For example, the polymorph can be characterized by one or two or three or four or five or six or seven or eight or nine of the peaks shown in Table 3.

TABLE 3

| Angle 2- | Intensity % |
|---|---|
| 6.8 | 35.5 |
| 10.1 | 30.7 |
| 10.6 | 53.1 |
| 13.6 | 46.0 |
| 14.2 | 63.8 |
| 17.2 | 26.4 |
| 18.4 | 34.0 |
| 19.2 | 100.0 |
| 23.5 | 3.8 |

In another embodiment, Form 3 can be characterized by the peaks identified at 2θ angles of 6.8, 10.6, 13.6, 14.2, and 19.2°. In another embodiment, Form 3 can be characterized by the peaks identified at 2θ angles of 10.6, 14.2, and 19.2°.

Form 4

Figure 4:
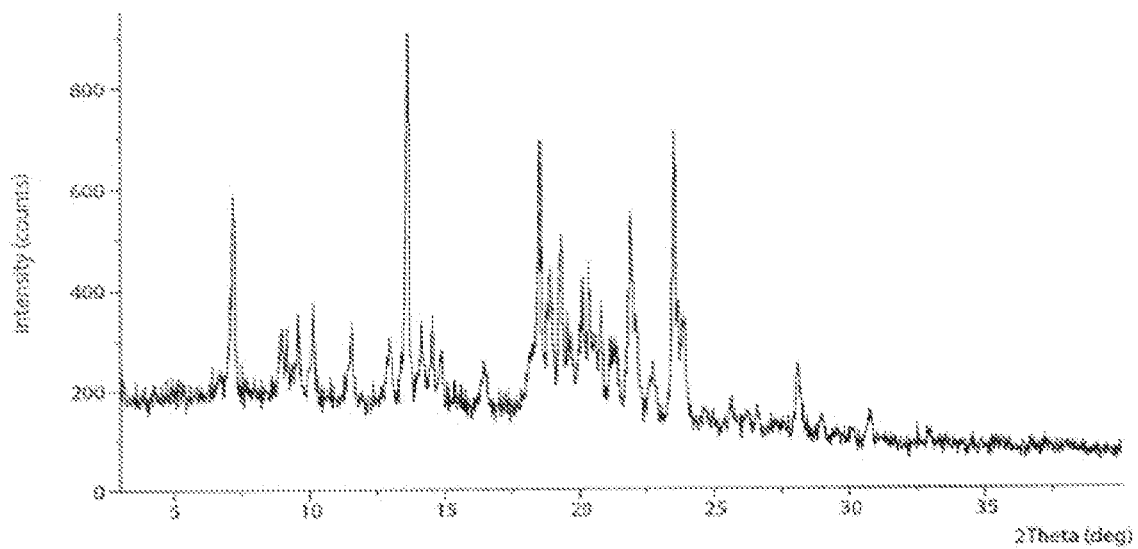
FIG. 4 is an X-ray powder diffractogram (XPRD) of COMPOUND 1 form 4.

In one embodiment, a single crystalline form, Form 4, of COMPOUND 1 is characterized by the X-ray powder diffraction (XRPD) pattern shown in FIG. 4, and data shown in Table 4, obtained using CuKα radiation. In a particular embodiment, the polymorph can be characterized by one or more of the peaks taken from FIG. 4, as shown in Table 4. For example, the polymorph can be characterized by one or two or three or four or five or six or seven or eight or nine of the peaks shown in Table 4.

TABLE 4

| Angle 2- | Intensity % |
|---|---|
| 7.2 | 53.3 |
| 10.1 | 26.7 |
| 11.5 | 20.5 |
| 13.6 | 100.0 |
| 18.5 | 72.0 |
| 19.3 | 46.9 |
| 20.3 | 39.4 |
| 21.9 | 55.4 |
| 23.5 | 77.5 |

In another embodiment, Form 4 can be characterized by the peaks identified at 2θ angles of 7.2, 13.6, 18.5, 19.3, 21.9, and 23.5°. In another embodiment, Form 4 can be characterized by the peaks identified at 2θ angles of 13.6, 18.5, and 23.5°.

Form 5

Figure 5:
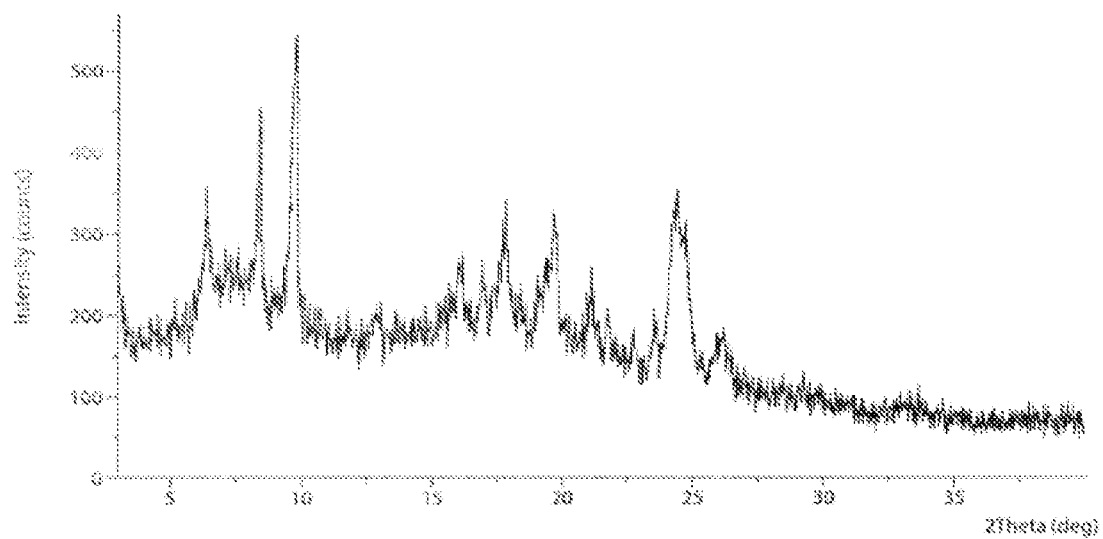
FIG. 5 is an X-ray powder diffractogram (XPRD) of COMPOUND 1 form 5.

In one embodiment, a single crystalline form, Form 5, of COMPOUND 1 is characterized by the X-ray powder diffraction (XRPD) pattern shown in FIG. 5, and data shown in Table 5, obtained using CuKα radiation. In a particular embodiment, the polymorph can be characterized by one or more of the peaks taken from FIG. 5, as shown in Table 5. For example, the polymorph can be characterized by one or two or three or four or five or six or seven or eight or nine of the peaks shown in Table 5.

TABLE 5

| Angle 2- | Intensity % |
|---|---|
| 6.4 | 45.4 |
| 8.4 | 84.0 |
| 9.8 | 100.0 |
| 16.1 | 26.0 |
| 16.9 | 22.7 |
| 17.8 | 43.6 |

TABLE 5-continued

| Angle 2- | Intensity % |
|---|---|
| 19.7 | 40.4 |
| 21.1 | 20.5 |
| 26.1 | 15.9 |

In another embodiment, Form 5 can be characterized by the peaks identified at 2θ angles of 6.4, 8.4, 9.8, 17.8, and 19.7°. In another embodiment, Form 5 can be characterized by the peaks identified at 2θ angles of 8.4 and 9.8°.

Form 6

Figure 6:
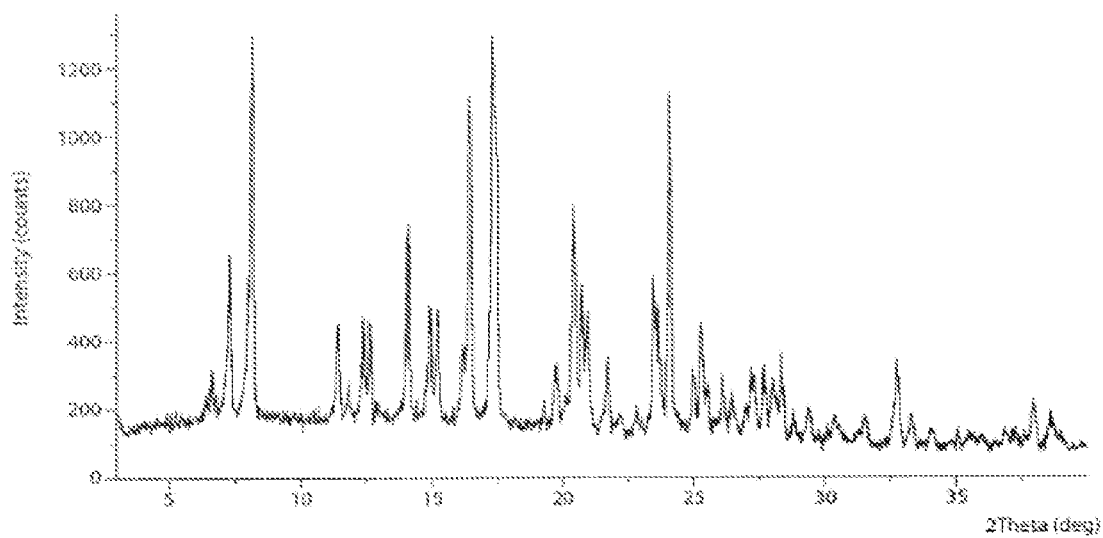
FIG. 6 is an X-ray powder diffractogram (XPRD) of COMPOUND 1 form 6.

In one embodiment, a single crystalline form, Form 6, of COMPOUND 1 is characterized by the X-ray powder diffraction (XRPD) pattern shown in FIG. 6, and data shown in Table 6, obtained using CuKα radiation. In a particular embodiment, the polymorph can be characterized by one or more of the peaks taken from FIG. 6, as shown in Table 6. For example, the polymorph can be characterized by one or two or three or four or five or six or seven or eight of the peaks shown in Table 6.

TABLE 6

| Angle 2- | Intensity % |
|---|---|
| 8.1 | 97.9 |
| 11.4 | 24.9 |
| 14.1 | 51.5 |
| 15.2 | 28.4 |
| 16.4 | 85.0 |
| 17.3 | 100.0 |
| 20.5 | 54.7 |
| 24.1 | 88.7 |

In another embodiment, Form 6 can be characterized by the peaks identified at 2θ angles of 8.1, 14.1, 16.4, 17.3, 20.5, and 24.1°. In another embodiment, Form 6 can be characterized by the peaks identified at 2θ angles of 8.1, 16.4, 17.3, and 24.1°.

Pharmaceutical Compositions and Routes of Administration

In one embodiment, the pharmaceutical composition provided herein comprises COMPOUND 1 and an excipient. In one embodiment, the pharmaceutical composition that comprises COMPOUND 1 and an excipient, is for oral administration. In one embodiment, the excipient is a diluent, a binder, a disintegrant, a wetting agent, a stabilizer, a glidant, and/or a lubricant. In one embodiment, the excipient is a diluent. In one embodiment, the excipient is a binder. In one embodiment, the excipient is a disintegrant. In one embodiment, the excipient is a wetting agent. In one embodiment, the excipient is a stabilizer. In one embodiment, the excipient is a glidant. In one embodiment, the excipient is a lubricant.

In one embodiment, the diluent is a microcrystalline cellulose.

In one embodiment, the binder is a hydroxypropyl cellulose.

In one embodiment, the disintegrant is sodium starch glycolate.

In one embodiment, the wetting agent is sodium lauryl sulfate.

In one embodiment, the stabilizer is hypromellose acetate succinate.

In one embodiment, the glidant is colloidal silicon dioxide.

In one embodiment, the lubricant is magnesiun stearate.

Pharmaceutical Compositions Containing Cytarabine

In certain embodiments, provided herein are pharmaceutical compositions comprising Cytarabine and a pharmaceutically acceptable carrier for administration to a patient in need thereof in the methods provided herein. In certain embodiments, the pharmaceutical composition comprises Cytarabine and a diluent or solvent. In certain embodiments, the pharmaceutical compositions comprising Cytarabine are for parenteral administration. In one embodiment, the pharmaceutical composition comprises Cytarabine in a sterile solution for intravenous, intrathecal or subcutaneous administration. In one embodiment, the pharmaceutical composition comprises Cytarabine in a sterile solution for intravenous administration. In one embodiment, the pharmaceutical composition comprises Cytarabine in a sterile solution for intrathecal administration. In one embodiment, the pharmaceutical composition comprises Cytarabine in a sterile solution for subcutaneous administration.

In certain embodiments, the pharmaceutical composition comprises an aqueous solution containing 20 mg/mL Cytarabine. In certain embodiments, the pharmaceutical composition comprises an aqueous solution containing 100 mg/mL Cytarabine.

In one embodiment, the pharmaceutical composition comprising Cytarabine contains no preservative. In one embodiment, the pharmaceutical composition comprising Cytarabine further comprises sodium chloride. In one embodiment, sodium chloride is present in about 0.68% based on total mass of the composition. In one embodiment, the pharmaceutical composition further comprises hydrochloric acid and/or sodium hydroxide to adjust the pH of the composition to about 7.2-7.8. In one embodiment, the pharmaceutical composition further comprises hydrochloric acid and/or sodium hydroxide to adjust the pH of the composition to about 7.3-7.7. In one embodiment, the pharmaceutical composition further comprises hydrochloric acid and/or sodium hydroxide to adjust the pH of the composition to about 7.4, 7.6 or 7.7.

In one embodiment, the pharmaceutical composition comprising Cytarabine contains a preservative. In one embodiment, the preservative is benzyl alcohol. In one embodiment, the amount of benzyl alcohol is about 0.9% based on total mass of the composition. In one embodiment, the pharmaceutical composition further comprises hydrochloric acid and/or sodium hydroxide to adjust the pH of the composition to about 7.6.

In certain embodiments, provided herein is a powder comprising Cytarabine, wherein the powder is suitable for reconstitution.

In certain embodiments, the composition is reconstituted with water containing 0.9% m/v benzyl alcohol.

In certain embodiments, Cytarabine is formulated and administered according to a package insert for cytarabine.

Pharmaceutical Compositions Containing Daunorubicin

In certain embodiments, provided herein are pharmaceutical compositions comprising Daunorubicin hydrochloride and a pharmaceutically acceptable carrier. In certain embodiments, the pharmaceutical composition comprises Daunorubicin and a diluent or solvent. In certain embodiments, the compositions are for intravenous administration to a patient in need thereof in the methods provided herein. In certain embodiments, the compositions further comprise sodium chloride. In certain embodiments, the compositions further comprise sodium hydroxide and/or hydrochloric acid to adjust the pH to 3-7. In certain embodiments, the compositions have a pH in the range 3-4, 4-5 or 4.5-6.5. In certain embodiments, the compositions comprise an aqueous solution of Daunorubicin hydrochloride equivalent to 5 mg/mL Daunorubicin, 9 mg/mL sodium chloride, sodium hydroxide and/or hydrochloric acid to adjust pH to 3-4.

In certain embodiments, Daunorubicin is formulated and administered per its package insert.

Pharmaceutical Compositions Containing Idarubicin

In certain embodiments, provided herein are pharmaceutical compositions comprising Idarubicin hydrochloride and a pharmaceutically acceptable carrier. In certain embodiments, the pharmaceutical composition comprises Idarubicin and a diluent or solvent. In certain embodiments, the compositions comprise Idarubicin hydrochloride as a sterile lyophilized powder for reconstitution and intravenous administration. In certain embodiments, the compositions comprise sterile lyophilized powder of Idarubicin hydrochloride in an amount of about 20 mg per single use vial. In certain embodiments, the compositions further comprise lactose NF.

In certain embodiments, provided herein are pharmaceutical compositions comprising Idarubicin hydrochloride in a sterile, semi-synthetic, preservative-free solution for intravenous administration. In certain embodiments, provided herein are pharmaceutical compositions comprising Idarubicin hydrochloride in isotonic parenteral preservative-free solution. In certain embodiment, the compositions are provided in single use vials.

In the one embodiment, the vials contain about 5 mL, 10 mL or 20 mL solution comprising Idarubicin hydrochloride. In certain embodiments, each vial contains idarubicin hydrochloride in an amount 1 mg/mL and the following inactive ingredients: glycerin, USP 25 mg/mL, water, hydrochloric acid, NF to adjust the pH to about 3.5.

In certain embodiments, each vial contains about 5 mg Idarubicin hydrochloride, 125 mg glycerol, water for injections q.s. to 5 mL and HCl to pH 3.5.

In certain embodiments, each vial contains about 10 mg Idarubicin hydrochloride, 250 mg glycerol, water for injections q.s. to 10 mL and HCl to pH 3.5.

In certain embodiments, Idarubicin is formulated and administered per its package insert.

Pharmaceutical Compositions Containing Mitoxantrone

In certain embodiments, provided herein are pharmaceutical compositions comprising Mitoxantrone hydrochloride and a pharmaceutically acceptable carrier. In certain embodiments, the pharmaceutical composition comprises Mitoxantrone and a diluent or solvent. In certain embodiments, the pharmaceutical compositions of Mitoxantrone hydrochloride are for intravenous administration.

In certain embodiments, the compositions are provided as a concentrate that requires dilution prior to injection. In certain embodiments, the composition is a sterile aqueous solution comprising Mitoxantrone hydrochloride equivalent to 2 mg/mL Mitoxantrone free base, sodium chloride (about 0.80% w/v), sodium acetate (about 0.005% w/v), glacial acetic acid (about 0.046% w/v), and water. In one embodiment, the composition has a pH of 3.0 to 4.5 and contains 0.14 mEq of sodium per mL. In certain embodiments, the composition does not contain any preservative.

In certain embodiments, Mitoxantrone is formulated and administered per its package insert.

Pharmaceutical Compositions Containing Etoposide

In certain embodiments, provided herein are pharmaceutical compositions comprising Etoposide phosphate and a pharmaceutically acceptable carrier. In certain embodiments, the pharmaceutical composition comprises Etoposide and a diluent or solvent. In certain embodiments, the pharmaceutical compositions of Etoposide phosphate are for intravenous infusion. In one embodiment, the pharmaceutical composition is provided in a single-dose vial containing Etoposide phosphate equivalent to about 100 mg Etoposide, about 32.7 mg sodium citrate USP, and about 300 mg dextran 40.

In certain embodiments, the pharmaceutical compositions of Etoposide phosphate are for intravenous injection. In one embodiment, the pharmaceutical compositions are provided as 20 mg/mL solutions in 100 mg (5 mL), 200 mg (10 mL) or 500 mg (25 mL) sterile, multiple dose vials, each mL containing about 20 mg Etoposide, about 2 mg citric acid, about 80 mg polysorbate 80, about 650 mg polyethylene glycol 300, and dehydrated alcohol about 33.2% (v/v).

In certain embodiments, Etoposide is formulated and administered per its package insert.

Pharmaceutically acceptable carriers, adjuvants and vehicles that may be used in the pharmaceutical compositions include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of COMPOUND 1 described herein.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Particular embodiments herein provide solid oral dosage forms that are tablets or capsules. In certain embodiments, the formulation is a tablet comprising COMPOUND 1. In certain embodiments, the formulation is a capsule comprising COMPOUND 1. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration.

In certain embodiments, embodiments herein encompass the use of COMPOUND 1 for the preparation of a pharmaceutical composition for treating a malignancy, characterized by the presence of a mutant allele of IDH2, wherein the composition is prepared for oral administration.

In certain embodiments, embodiments herein encompass the use of Cytarabine, Daunorubicin, Idarubicin, Mitoxantrone, and/or Etoposide for the preparation of a pharmaceutical composition for treating a malignancy, characterized by the presence of a mutant allele of IDH2, wherein the composition is prepared for intravenous administration.

The methods herein contemplate administration of an effective amount of a compound or a pharmaceutical composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

In one embodiment, provided herein are methods of treating acute myeloid leukemia (AML), characterized by the presence of a mutant allele of IDH2, by administering to a subject a therapeutically effective amount of a combination of a mutant IDH2 inhibitor and an AML induction and consolidation therapy.

In one embodiment, the mutant IDH2 inhibitor is 2-methyl-1-[(4-[6-(trifluoromethyl)pyridin-2-yl]-6-{[2-(trifluoromethyl)pyridin-4-yl]amino}-1,3,5-triazin-2-yl) amino]propan-2-ol, or a pharmaceutically acceptable salt, solvate, tautomer, stereoisomer, isotopologue, prodrug, metabolite, or a polymorph thereof (COMPOUND 1).

In one embodiment, provided herein is a method of treating AML characterized by the presence of a mutant allele of IDH2, comprising administering to a subject a therapeutically effective amount of COMPOUND 1 and the AML induction therapy and consolidation therapy.

In one embodiment, provided herein is a method of treating AML characterized by the presence of a mutant allele of IDH2, comprising administering to a subject a pharmaceutical composition comprising a therapeutically effective amount of COMPOUND 1 and the AML induction therapy and consolidation therapy.

In one embodiment, provided herein is a method of treating AML selected from newly diagnosed AML, previously untreated AML, AML arising from myelodysplastic syndrome (MDS), AML arising from antecedent hematologic disorder (AHD) and AML arising after exposure to genotoxic injury. In certain embodiments, the genotoxic injury is resulting from radiation and/or chemotherapy. In one embodiment, provided herein is a method of treating AML arising after exposure to genotoxic injury resulting from radiation and/or chemotherapy.

In one embodiment, provided herein is a method of treating newly diagnosed AML.

In one embodiment, provided herein is a method of treating previously untreated AML.

In one embodiment, provided herein is a method of treating AML arising from myelodysplastic syndrome (MDS).

In one embodiment, provided herein is a method of treating AML arising from antecedent hematologic disorder (AHD).

In one embodiment, provided herein is a method of treating AML arising after exposure to genotoxic injury.

In one embodiment, the AML induction therapy is a combination of Cytarabine and Daunorubicin. In one embodiment, the AML induction therapy is a combination of Cytarabine and Idarubicin.

In one embodiment, the AML consolidation therapy is Cytarabine. In one embodiment, the AML consolidation therapy is a combination of Mitoxantrone and Etoposide.

In one embodiment, the method of treating AML provided herein comprises administering a therapeutically effective amount of COMPOUND 1 orally and Cytarabine and Daunorubicin intravenously during the induction stage, followed by administering a therapeutically effective amount of COMPOUND 1 orally and Cytarabine intravenously during the consolidation stage.

In one embodiment, the method of treating AML provided herein comprises administering a therapeutically effective amount of COMPOUND 1 orally and Cytarabine and Idarubicin intravenously during the induction stage, followed by administering a therapeutically effective amount of COMPOUND 1 orally and Cytarabine intravenously during the consolidation stage.

In one embodiment, the method of treating AML provided herein comprises administering a therapeutically effective amount of COMPOUND 1 orally and Cytarabine and Daunorubicin intravenously during the induction stage followed by administering a therapeutically effective amount of COMPOUND 1 orally and Mitoxantrone and Etoposide intravenously during the consolidation stage.

In one embodiment, the method of treating AML provided herein comprises administering a therapeutically effective amount of COMPOUND 1 orally and Cytarabine and Idarubicin intravenously during the induction stage, followed by administering a therapeutically effective amount of COMPOUND 1 orally and Mitoxantrone and Etoposide intravenously during the consolidation stage.

In one embodiment, COMPOUND 1, Cytarabine, and Daunorubicin are administered concurrently. In one embodiment, COMPOUND 1, Cytarabine, and Daunorubicin are administered sequentially. In one embodiment, COMPOUND 1, Cytarabine, and Idarubicin are administered concurrently. In one embodiment, COMPOUND 1, Cytarabine, and Idarubicin are administered sequentially.

In one embodiment, the malignancy to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

A malignancy can be analyzed by sequencing cell samples to determine the presence and specific nature of (e.g., the changed amino acid present at) a mutation at amino acid 140 and/or 172 of IDH2.

Without being bound by theory, applicants have found that mutant alleles of IDH2, wherein the IDH2 mutation results in a new ability of the enzyme to catalyze the NADPH-dependent reduction of α ketoglutarate to R( ) 2 hydroxyglutarate, and in particular R140Q and/or R172K mutations of IDH2, characterize a subset of all types of cancers, without regard to their cellular nature or location in the body. Thus, the compounds, compositions and methods provided herein are useful to treat any type of cancer that is characterized by the presence of a mutant allele of IDH2 imparting such activity and in particular an IDH2 R140Q and/or R172K mutation In one embodiment the malignancy is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well-known determinations of efficacy of malignancy treatment, such as reduction in number and size of tumors and/or other cancer-associated lesions, improvement in the general health of the subject, and alterations in other biomarkers that are associated with malignancy treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 µm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

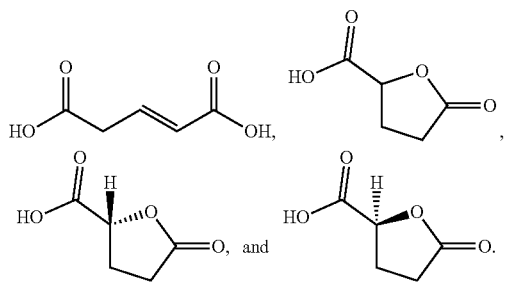

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by Mill and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Thus, according to another embodiment, provided herein is a method of treating 2-hydroxyglutaric aciduria, particularly D-2-hydroxyglutaric aciduria, in a subject by administering to the subject COMPOUND 1, Cytarabine, and Daunorubicin. In one embodiment, provided herein is a method of treating 2-hydroxyglutaric aciduria, particularly D-2-hydroxyglutaric aciduria, in a subject by administering to the subject COMPOUND 1, Cytarabine, and Idarubicin.

In one embodiment, prior to and/or after treatment with COMPOUND 1, Cytarabine, and Daunorubicin, the method further comprises the step of evaluating the growth, size, weight, invasiveness, stage and/or other phenotype of the malignancy. In one embodiment, prior to and/or after treatment with COMPOUND 1, Cytarabine, and Idarubicin, the method further comprises the step of evaluating the growth, size, weight, invasiveness, stage and/or other phenotype of the malignancy.

In one embodiment, prior to and/or after treatment with COMPOUND 1, Cytarabine, and Daunorubicin, the method further comprises the step of evaluating the IDH2 genotype of the malignancy. In one embodiment, prior to and/or after treatment with COMPOUND 1, Cytarabine, and Idarubicin, the method further comprises the step of evaluating the IDH2 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 1, Cytarabine, and Daunorubicin, the method further comprises the step of determining the 2HG level in the subject. In one embodiment, prior to and/or after treatment with COMPOUND 1, Cytarabine, and Idarubicin, the method further comprises the step of determining the 2HG level in the subject. This may be achieved by spectroscopic analysis, e.g., magnetic resonance-based analysis, e.g., MM and/or MRS measurement, sample analysis of bodily fluid, such as serum or spinal cord fluid analysis, or by analysis of surgical material, e.g., by mass-spectroscopy.

In one embodiment, depending on the disease to be treated and the subject's condition, COMPOUND 1 may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. COMPOUND 1 may be formulated in suitable dosage unit with pharmaceutically acceptable excipients, carriers, adjuvants and vehicles, appropriate for each route of administration. In one embodiment, COMPOUND 1 is administered orally.

In one embodiment, the amount of COMPOUND 1 administered in the methods provided herein may range, e.g., between about 10 mg/m$^2$ and 2000 mg/m$^2$. In one embodiment, the range is between about 50 mg/m$^2$ and 1000 mg/m$^2$. In one embodiment, the range is between about 100 mg/m$^2$ and 500 mg/m$^2$. In one embodiment, the range is between about 150 mg/m$^2$ and 300 mg/m$^2$. In one embodiment, the range is between about 200 mg/m$^2$ and 250 mg/m$^2$.

In certain embodiments, particular dosages are, e.g., about 10 mg/m$^2$. In one embodiment, the dose is about 25 mg/m$^2$. In one embodiment, the dose is about 50 mg/m$^2$. In one embodiment, the dose is about 75 mg/m$^2$. In one embodiment, the dose is about 100 mg/m$^2$. In one embodiment, the dose is about 125 mg/m$^2$. In one embodiment, the dose is about 150 mg/m$^2$. In one embodiment, the dose is about 175 mg/m$^2$. In one embodiment, the dose is about 200 mg/m$^2$. In one embodiment, the dose is about 225 mg/m$^2$. In one embodiment, the dose is about 250 mg/m$^2$. In one embodiment, the dose is about 275 mg/m$^2$. In one embodiment, the dose is about 300 mg/m$^2$. In one embodiment, the dose is about 50 mg/m$^2$. In one embodiment, the dose is about 400 mg/m$^2$.

In one embodiment, the amount of COMPOUND 1 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 1 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 1 can be delivered as a single dose such as, e.g., a single bolus injection, or oral tablets or pills; or over time such as, e.g., continuous infusion over time or divided bolus doses over time. In one embodiment, COMPOUND 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 1 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 1 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 1 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of COMPOUND 1 administered to a subject in need thereof for 28 days. In one embodiment, treatment cycles comprise multiple doses of COMPOUND 1 administered to a subject in need thereof for greater than 28 days.

In one embodiment, depending on the disease to be treated and the subject's condition, Cytarabine may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Cytarabine may be formulated in suitable dosage unit with pharmaceutically acceptable excipients, carriers, adjuvants and vehicles, appropriate for each route of administration. In one embodiment, Cytarabine is administered intravenously.

In certain embodiments, treatment cycles comprise multiple doses of Cytarabine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of Cytarabine administered to a subject in need thereof over 2 to 10 days. In one embodiment, treatment cycles comprise multiple doses of Cytarabine administered to a subject in need thereof over 4 to 8 days. In one embodiment, treatment cycles comprise multiple doses of Cytarabine administered to a subject in need thereof for 4 days. In one embodiment, treatment cycles comprise multiple doses of Cytarabine administered to a subject in need thereof for 5 days. In one embodiment, treatment cycles comprise multiple doses of Cytarabine administered to a subject in need thereof for 6 days. In one embodiment, treatment cycles comprise multiple doses of Cytarabine administered to a subject in need thereof for 7 days. In one embodiment, treatment cycles comprise multiple doses of Cytarabine administered to a subject in need thereof for 8 days. In one embodiment, treatment cycles comprise multiple doses of Cytarabine administered to a subject in need thereof for 9 days. In one embodiment, treatment cycles comprise multiple doses of Cytarabine administered to a subject in need thereof for 10 days.

Suitable dosage amounts for the methods provided herein include, e.g., therapeutically effective amounts and prophylactically effective amounts of Cytarabine. For example, in certain embodiments, the amount of Cytarabine administered during the induction stage in the methods provided herein may range, e.g., between about 10 $mg/m^2/day$ and about 1,500 $mg/m^2/day$. In certain embodiments, the amount of Cytarabine is between about 50 $mg/m^2/day$ and about 1,000 $mg/m^2/day$. In certain embodiments, the amount of Cytarabine is between about 100 $mg/m^2/day$ and about 500 $mg/m^2/day$. In certain embodiments, the amount of Cytarabine is between about 150 $mg/m^2/day$ and about 300 $mg/m^2/day$. In certain embodiments, the amount of Cytarabine is between about 150 $mg/m^2/day$ and about 200 $mg/m^2/day$. In certain embodiments, the particular dosage is about 50 $mg/m^2/day$. In one embodiment, the particular dosage is about 75 $mg/m^2/day$. In one embodiment, the particular dosage is about 100 $mg/m^2/day$. In one embodiment, the particular dosage is about 125 $mg/m^2/day$. In one embodiment, the particular dosage is about 150 $mg/m^2/day$. In one embodiment, the particular dosage is about 175 $mg/m^2/day$. In one embodiment, the particular dosage is about 200 $mg/m^2/day$. In one embodiment, the particular dosage is about 225 $mg/m^2/day$. In one embodiment, the particular dosage is about 250 $mg/m^2/day$. In one embodiment, the particular dosage is about 275 $mg/m^2/day$. In one embodiment, the particular dosage is about 300 $mg/m^2/day$. In one embodiment, the particular dosage is about 350 $mg/m^2/day$. In one embodiment, the particular dosage is about 400 $mg/m^2/day$. In certain embodiments, the particular dosage is up to about 100 $mg/m^2/day$. In one embodiment, the particular dosage is up to about 125 $mg/m^2/day$. In one embodiment, the particular dosage is up to about 150 $mg/m^2/day$. In one embodiment, the particular dosage is up to about 175 $mg/m^2/day$. In one embodiment, the particular dosage is up to about 200 $mg/m^2/day$. In one embodiment, the particular dosage is up to about 225 $mg/m^2/day$. In one embodiment, the particular dosage is up to about 250 $mg/m^2/day$. In one embodiment, the particular dosage is up to about 275 $mg/m^2/day$. In one embodiment, the particular dosage is up to about 300 $mg/m^2/day$. In one embodiment, the particular dosage is up to about 350 $mg/m^2/day$. In one embodiment, the particular dosage is up to about 400 $mg/m^2/day$.

In certain embodiments, the amount of Cytarabine administered during the consolidation stage in the methods provided herein may range, e.g., between about 0.1 $g/m^2/day$ and about 25 $g/m^2/day$. For example, in certain embodiments, the amount of Cytarabine administered in the methods provided herein may range, e.g., between about 0.5 g/m²/day and about 15 g/m²/day. In certain embodiments, the amount of Cytarabine is between about 1 g/m²/day and about 10 g/m²/day. In certain embodiments, the amount of Cytarabine is between about 1 g/m²/day and about 5 g/m²/day. In certain embodiments, the amount of Cytarabine is between about 1 g/m²/day and about 3 g/m²/day. In certain embodiments, the amount of Cytarabine is between about 1 g/m²/day and about 2 g/m²/day. In certain embodiments, the amount of Cytarabine is between about 1 g/m²/day and about 1.5 g/m²/day. In certain embodiments, the amount of Cytarabine is between about 2 g/m²/day and about 3 g/m²/day. In certain embodiments, the particular dosage of Cytarabine is about 0.1 g/m²/day. In one embodiment, the particular dosage is about 0.5 g/m²/day. In one embodiment, the particular dosage is about 1 g/m²/day. In one embodiment, the particular dosage is about 1.5 g/m²/day. In one embodiment, the particular dosage is about 2 g/m²/day. In one embodiment, the particular dosage is about 2.5 g/m²/day. In one embodiment, the particular dosage is about 3 g/m²/day. In one embodiment, the particular dosage is about 4 g/m²/day. In one embodiment, the particular dosage is about 5 g/m²/day. In certain embodiments, the particular dosage of Cytarabine is up to about 0.1 g/m²/day. In one embodiment, the particular dosage is up to about 0.5 g/m²/day. In one embodiment, the particular dosage is up to about 1 g/m²/day. In one embodiment, the particular dosage is up to about 1.5 g/m²/day. In one embodiment, the particular dosage is up to about 2 g/m²/day. In one embodiment, the particular dosage is up to about 2.5 g/m²/day. In one embodiment, the particular dosage is up to about 3 g/m²/day. In one embodiment, the particular dosage is up to about 4 g/m²/day. In one embodiment, the particular dosage is up to about 5 g/m²/day.

In one embodiment, depending on the disease to be treated and the subject's condition, Daunorubicine may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Daunorubicine may be formulated in suitable dosage unit with pharmaceutically acceptable excipients, carriers, adjuvants and vehicles, appropriate for each route of administration. In one embodiment, Daunorubicine is administered intravenously.

In certain embodiments, treatment cycles comprise multiple doses of Daunorubicine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of Daunorubicine administered to a subject in need thereof over 1 to 8 days. In one embodiment, treatment cycles comprise multiple doses of Daunorubicine administered to a subject in need thereof over 2 to 6 days. In one embodiment, treatment cycles comprise multiple doses of Daunorubicine administered to a subject in need thereof for 2 days. In one embodiment, treatment cycles comprise multiple doses of Daunorubicine administered to a subject in need thereof for 3 days. In one embodiment, treatment cycles comprise multiple doses of Daunorubicine administered to a subject in need thereof for 4 days. In one embodiment, treatment cycles comprise multiple doses of Daunorubicine administered to a subject in need thereof for 5 days.

Suitable dosage amounts for the methods provided herein include, e.g., therapeutically effective amounts and prophylactically effective amounts of Daunorubicine. For example, in certain embodiments, the amount of Daunorubicine administered in the methods provided herein may range, e.g., between about 1 mg/m²/day and about 500 mg/m²/day. In certain embodiments, the amount of Daunorubicine is between about 10 mg/m²/day and about 300/m²/day. In certain embodiments, the amount of Daunorubicine is between about 20 g/m²/day and about 200 g/m²/day. In certain embodiments, the amount of Daunorubicine is between about 30 mg/m²/day and about 150 mg/m²/day. In certain embodiments, the amount of Daunorubicine is between about 40 mg/m²/day and about 120 mg/m²/day. In certain embodiments, the amount of Daunorubicine is between about 50 mg/m²/day and about 100 mg/m²/day. In certain embodiments, the amount of a Daunorubicine is between about 60 mg/m²/day and about 90 mg/m²/day. In certain embodiments, the amount of Daunorubicine is between about 70 mg/m²/day and about 80 mg/m²/day.

In certain embodiments, the particular dosage of Daunorubicine is about 10 mg/m²/day. In one embodiment, the particular dosage is about 15 mg/m²/day. In one embodiment, the particular dosage is about 20 mg/m²/day. In one embodiment, the particular dosage is about 25 mg/m²/day. In one embodiment, the particular dosage is about 30 mg/m²/day. In one embodiment, the particular dosage is about 35 mg/m²/day. In one embodiment, the particular dosage is about 40 mg/m²/day. In one embodiment, the particular dosage is about 45 mg/m²/day. In one embodiment, the particular dosage is about 50 mg/m²/day. In one embodiment, the particular dosage is about 55 mg/m²/day. In one embodiment, the particular dosage is about 60 mg/m²/day. In one embodiment, the particular dosage is about 65 mg/m²/day. In one embodiment, the particular dosage is about 70 mg/m²/day. In one embodiment, the particular dosage is about 80 mg/m²/day. In one embodiment, the particular dosage is about 90 mg/m²/day. In one embodiment, the particular dosage is about 100 mg/m²/day.

In certain embodiments, the particular dosage of of Daunorubicine is up to about 10 mg/m²/day. In one embodiment, the particular dosage is up to about 15 mg/m²/day. In one embodiment, the particular dosage is up to about 20 mg/m²/day. In one embodiment, the particular dosage is up to about 25 mg/m²/day. In one embodiment, the particular dosage is up to about 30 mg/m²/day. In one embodiment, the particular dosage is up to about 35 mg/m²/day. In one embodiment, the particular dosage is up to about 40 mg/m²/day. In one embodiment, the particular dosage is up to about 45 mg/m²/day. In one embodiment, the particular dosage is up to about 50 mg/m²/day. In one embodiment, the particular dosage is up to about 55 mg/m²/day. In one embodiment, the particular dosage is up to about 60 mg/m²/day. In one embodiment, the particular dosage is up to about 70 mg/m²/day. In one embodiment, the particular dosage is up to about 80 mg/m²/day. In one embodiment, the particular dosage is up to about 90 mg/m²/day. In one embodiment, the particular dosage is up to about 100 mg/m²/day.

In one embodiment, depending on the disease to be treated and the subject's condition, Idarubicine may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Daunorubicine may be formulated in suitable dosage unit with pharmaceutically acceptable excipients, carriers, adjuvants and vehicles, appropriate for each route of administration. In one embodiment, Daunorubicine is administered intravenously.

In certain embodiments, treatment cycles comprise multiple doses of Idarubicine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of Idarubicine administered to a subject in need thereof over 1 to 8 days. In one embodiment, treatment cycles comprise multiple doses of Idarubicine administered to a subject in need thereof over 2 to 6 days. In one embodiment, treatment cycles comprise multiple doses of Idarubicine administered to a subject in need thereof for 2 days. In one embodiment, treatment cycles comprise multiple doses of Idarubicine administered to a subject in need thereof for 3 days. In one embodiment, treatment cycles comprise multiple doses of Idarubicine administered to a subject in need thereof for 4 days. In one embodiment, treatment cycles comprise multiple doses of Idarubicine administered to a subject in need thereof for 5 days.

Suitable dosage amounts for the methods provided herein include, e.g., therapeutically effective amounts and prophylactically effective amounts of Idarubicine. For example, in certain embodiments, the amount of Idarubicine administered in the methods provided herein may range, e.g., between about 0.5 mg/m$^2$/day and about 50 mg/m$^2$/day. In certain embodiments, the amount of Idarubicine is between about 1 mg/m$^2$/day and about 25/m$^2$/day. In certain embodiments, the amount of Idarubicine is between about 2 mg/m$^2$/day and about 20 mg/m$^2$/day. In certain embodiments, the amount of Idarubicine is between about 3 mg/m$^2$/day and about 15 mg/m$^2$/day. In certain embodiments, the amount of Idarubicine is between about 5 mg/m$^2$/day and about 14 mg/m$^2$/day. In certain embodiments, the amount of Idarubicine is between about 10 mg/m$^2$/day and about 13 mg/m$^2$/day.

In certain embodiments, the particular dosage of Idarubicine is about 1 mg/m$^2$/day. In one embodiment, the particular dosage is about 2 mg/m$^2$/day. In one embodiment, the particular dosage is about 3 mg/m$^2$/day. In one embodiment, the particular dosage is about 4 mg/m$^2$/day. In one embodiment, the particular dosage is about 5 mg/m$^2$/day. In one embodiment, the particular dosage is about 6 mg/m$^2$/day. In one embodiment, the particular dosage is about 7 mg/m$^2$/day. In one embodiment, the particular dosage is about 8 mg/m$^2$/day. In one embodiment, the particular dosage is about 9 mg/m$^2$/day. In one embodiment, the particular dosage is about 10 mg/m$^2$/day. In one embodiment, the particular dosage is about 11 mg/m$^2$/day. In one embodiment, the particular dosage is about 12 mg/m$^2$/day. In one embodiment, the particular dosage is about 13 mg/m$^2$/day. In one embodiment, the particular dosage is about 14 mg/m$^2$/day. In one embodiment, the particular dosage is about 15 mg/m$^2$/day. In one embodiment, the particular dosage is about 16 mg/m$^2$/day. In one embodiment, the particular dosage is about 17 mg/m$^2$/day. In one embodiment, the particular dosage is about 18 mg/m$^2$/day. In one embodiment, the particular dosage is about 19 mg/m$^2$/day. In one embodiment, the particular dosage is about 120 mg/m$^2$/day.

In certain embodiments, the particular dosage of Idarubicine is up to about 1 mg/m$^2$/day. In one embodiment, the particular dosage is up to about 2 mg/m$^2$/day. In one embodiment, the particular dosage is up to about 3 mg/m$^2$/day. In one embodiment, the particular dosage is up to about 4 mg/m$^2$/day. In one embodiment, the particular dosage is up to about 5 mg/m$^2$/day. In one embodiment, the particular dosage is up to about 6 mg/m$^2$/day. In one embodiment, the particular dosage is up to about 7 mg/m$^2$/day. In one embodiment, the particular dosage is up to about 8 mg/m$^2$/day. In one embodiment, the particular dosage is up to about 9 mg/m$^2$/day. In one embodiment, the particular dosage is up to about 10 mg/m$^2$/day. In one embodiment, the particular dosage is up to about 11 mg/m$^2$/day. In one embodiment, the particular dosage is up to about 12 mg/m$^2$/day. In one embodiment, the particular dosage is up to about 13 mg/m$^2$/day. In one embodiment, the particular dosage is up to about 14 mg/m$^2$/day. In one embodiment, the particular dosage is up to about 15 mg/m$^2$/day. In one embodiment, the particular dosage is up to about 16 mg/m$^2$/day. In one embodiment, the particular dosage is up to about 17 mg/m$^2$/day. In one embodiment, the particular dosage is up to about 18 mg/m$^2$/day. In one embodiment, the particular dosage is up to about 19 mg/m$^2$/day. In one embodiment, the particular dosage is up to about 20 mg/m$^2$/day.

In one embodiment, depending on the disease to be treated and the subject's condition, Mitoxantrone may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Mitoxantrone may be formulated in suitable dosage unit with pharmaceutically acceptable excipients, carriers, adjuvants and vehicles, appropriate for each route of administration. In one embodiment, Mitoxantrone is administered intravenously.

In certain embodiments, treatment cycles comprise multiple doses of Mitoxantrone administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of Mitoxantrone administered to a subject in need thereof over 1 to 15 days. In one embodiment, treatment cycles comprise multiple doses of Mitoxantrone administered to a subject in need thereof over 2 to 10 days. In one embodiment, treatment cycles comprise multiple doses of Mitoxantrone administered to a subject in need thereof for 2 days. In one embodiment, treatment cycles comprise multiple doses of Mitoxantrone administered to a subject in need thereof for 3 days. In one embodiment, treatment cycles comprise multiple doses of Mitoxantrone administered to a subject in need thereof for 4 days. In one embodiment, treatment cycles comprise multiple doses of Mitoxantrone administered to a subject in need thereof for 5 days. In one embodiment, treatment cycles comprise multiple doses of Mitoxantrone administered to a subject in need thereof for 6 days. In one embodiment, treatment cycles comprise multiple doses of Mitoxantrone administered to a subject in need thereof for 7 days. In one embodiment, treatment cycles comprise multiple doses of Mitoxantrone administered to a subject in need thereof for 8 days.

Suitable dosage amounts for the methods provided herein include, e.g., therapeutically effective amounts and prophylactically effective amounts of Mitoxantrone. For example, in certain embodiments, the amount of Mitoxantrone administered in the methods provided herein may range, e.g., between about 0.5 mg/m$^2$/day and about 50 mg/m$^2$/day. In certain embodiments, the amount of Mitoxantrone is between about 1 mg/m$^2$/day and about 25/m$^2$/day. In certain embodiments, the amount of Mitoxantrone is between about 5 mg/m$^2$/day and about 20 mg/m$^2$/day. In certain embodiments, the amount of Mitoxantrone is between about 10 mg/m$^2$/day and about 15 mg/m$^2$/day.

In certain embodiments, the particular dosage of Mitoxantrone is about 1 mg/m$^2$/day. In one embodiment, the particular dosage is about 2 mg/m$^2$/day. In one embodiment, the particular dosage is about 3 mg/m$^2$/day. In one embodiment, the particular dosage is about 4 mg/m$^2$/day. In one embodiment, the particular dosage is about 5 mg/m$^2$/day. In one embodiment, the particular dosage is about 6 mg/m$^2$/day. In one embodiment, the particular dosage is about 7 mg/m$^2$/day. In one embodiment, the particular dosage is about 8 mg/m$^2$/day. In one embodiment, the particular dosage is about 9 mg/m$^2$/day. In one embodiment, the particular dosage is about 10 mg/m$^2$/day. In one embodiment, the particular dosage is about 11 mg/m$^2$/day. In one embodiment, the particular dosage is about 12 mg/m$^2$/day. In one embodiment, the particular dosage is about 13 mg/m$^2$/day. In one embodiment, the particular dosage is about 14 mg/m$^2$/day. In one embodiment, the particular dosage is about 15 mg/m$^2$/day. In one embodiment, the particular dosage is about 16 mg/m$^2$/day. In one embodiment, the particular dosage is about 17 mg/m$^2$/day. In one embodiment, the particular dosage is about 18 mg/m$^2$/day. In one embodiment, the particular dosage is about 19 mg/m$^2$/day. In one embodiment, the particular dosage is about 20 mg/m$^2$/day.

In certain embodiments, the particular dosage of Mitoxantrone is up to about 1 mg/m$^2$/day. In one embodiment, the particular dosage is up to about 2 mg/m$^2$/day. In one embodiment, the particular dosage is up to about 3 mg/m$^2$/day. In one embodiment, the particular dosage is up to about 4 mg/m$^2$/day. In one embodiment, the particular dosage is up to about 5 mg/m$^2$/day. In one embodiment, the particular dosage is up to about 6 mg/m$^2$/day. In one embodiment, the particular dosage is up to about 7 mg/m$^2$/day. In one embodiment, the particular dosage is up to about 8 mg/m$^2$/day. In one embodiment, the particular dosage is up to about 9 mg/m$^2$/day. In one embodiment, the particular dosage is up to about 10 mg/m$^2$/day. In one embodiment, the particular dosage is up to about 11 mg/m$^2$/day. In one embodiment, the particular dosage is up to about 12 mg/m$^2$/day. In one embodiment, the particular dosage is up to about 13 mg/m$^2$/day. In one embodiment, the particular dosage is up to about 14 mg/m$^2$/day. In one embodiment, the particular dosage is up to about 15 mg/m$^2$/day. In one embodiment, the particular dosage is up to about 16 mg/m$^2$/day. In one embodiment, the particular dosage is up to about 17 mg/m$^2$/day. In one embodiment, the particular dosage is up to about 18 mg/m$^2$/day. In one embodiment, the particular dosage is up to about 19 mg/m$^2$/day. In one embodiment, the particular dosage is up to about 20 mg/m$^2$/day.

In one embodiment, depending on the disease to be treated and the subject's condition, Etoposide may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Etoposide may be formulated in suitable dosage unit with pharmaceutically acceptable excipients, carriers, adjuvants and vehicles, appropriate for each route of administration. In one embodiment, Etoposide is administered intravenously. In one embodiment, Etoposide is administered orally.

In certain embodiments, treatment cycles comprise multiple doses of Etoposide administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). In one embodiment, treatment cycles comprise multiple doses of Etoposide administered to a subject in need thereof over 1 to 15 days. In one embodiment, treatment cycles comprise multiple doses of Etoposide administered to a subject in need thereof over 2 to 10 days. In one embodiment, treatment cycles comprise multiple doses of Etoposide administered to a subject in need thereof for 2 days. In one embodiment, treatment cycles comprise multiple doses of Etoposide administered to a subject in need thereof for 3 days. In one embodiment, treatment cycles comprise multiple doses of Mitoxantrone administered to a subject in need thereof for 4 days. In one embodiment, treatment cycles comprise multiple doses of Mitoxantrone administered to a subject in need thereof for 5 days. In one embodiment, treatment cycles comprise multiple doses of Mitoxantrone administered to a subject in need thereof for 6 days. In one embodiment, treatment cycles comprise multiple doses of Mitoxantrone administered to a subject in need thereof for 7 days. In one embodiment, treatment cycles comprise multiple doses of Mitoxantrone administered to a subject in need thereof for 8 days.

Suitable dosage amounts for the methods provided herein include, e.g., therapeutically effective amounts and prophylactically effective amounts of Etoposide. For example, in certain embodiments, the amount of Etoposide administered in the methods provided herein may range, e.g., between about 10 mg/m$^2$/day and about 1000 mg/m$^2$/day. In certain embodiments, the amount of Etoposide is between about 50 mg/m$^2$/day and about 500/m$^2$/day. In certain embodiments, the amount of Etoposide is between about 75 mg/m$^2$/day and about 250 mg/m$^2$/day. In certain embodiments, the amount of Etoposide is between about 100 mg/m$^2$/day and about 200 mg/m$^2$/day.

In certain embodiments, the particular dosage of Etoposide is about 10 mg/m$^2$/day. In one embodiment, the particular dosage is about 25 mg/m$^2$/day. In one embodiment, the particular dosage is about 50 mg/m$^2$/day. In one embodiment, the particular dosage is about 75 mg/m$^2$/day. In one embodiment, the particular dosage is about 100 mg/m$^2$/day. In one embodiment, the particular dosage is about 125 mg/m$^2$/day. In one embodiment, the particular dosage is about 150 mg/m$^2$/day. In one embodiment, the particular dosage is about 175 mg/m$^2$/day. In one embodiment, the particular dosage is about 200 mg/m$^2$/day.

In certain embodiments, the particular dosage of Etoposide is up to about 10 mg/m$^2$/day. In one embodiment, the particular dosage is up to about 25 mg/m$^2$/day. In one embodiment, the particular dosage is up to about 50 mg/m$^2$/day. In one embodiment, the particular dosage is up to about 75 mg/m$^2$/day. In one embodiment, the particular dosage is up to about 100 mg/m$^2$/day. In one embodiment, the particular dosage is up to about 125 mg/m$^2$/day. In one embodiment, the particular dosage is up to about 150 mg/m$^2$/day. In one embodiment, the particular dosage is up to about 175 mg/m$^2$/day. In one embodiment, the particular dosage is up to about 200 mg/m$^2$/day.

In one embodiment, a method provided herein comprises administering the COMPOUND 1 and the induction therapy in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, a method provided herein comprises administering the COMPOUND 1 and the consolidation therapy in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or greater than 30 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, COMPOUND 1 is administered orally once a day. In one embodiment, COMPOUND 1 is administered on days 1-28 of each 28-day cycle. In one embodiment, 50 mg of COMPOUND 1 is administered orally once a day. In another embodiment, 100 mg of COMPOUND 1 is administered orally once a day. In yet another embodiment, 200 mg of COMPOUND 1 is administered orally once a day.

In one embodiment, the induction therapy comprises Cytarabine administered for 7 days and Daunorubicin administered for 3 days. In one embodiment, the induction therapy comprises Cytarabine administered for 7 days and Idarubicin administered for 3 days.

In one embodiment, in the methods provided herein, the induction cycle may be repeated no later than 35 days from the previous induction cycle. In one embodiment, in the methods provided herein, the induction cycle may be repeated not earlier than 14 days after bone marrow aspirate/biopsy. In one embodiment, in the methods provided herein, the induction cycle may be repeated by administering Cytarabine for 5 days and Daunorubicin or Idarubicin for 2 days starting no later than 35 days from the previous induction cycle. In one embodiment, in the methods provided herein, the induction cycle may be repeated by administering Cytarabine for 5 days and Daunorubicin or Idarubicin for 2 days starting not earlier than 14 days after bone marrow aspirate/biopsy.

In one embodiment, the consolidation therapy comprises Cytarabine administered for 3 days. In one embodiment, the consolidation therapy comprises Cytarabine administered on days 1, 3, and 5 of the cycle. In one embodiment, the consolidation therapy comprises Mitoxantrone and Etoposide administered for 5 days. In one embodiment, in the methods provided herein, the consolidation cycle can be performed within 28-42 days.

EXAMPLES

Example 1. Phase a Phase 1, Multicenter, Open-Label, Safety Study of Compound 1 and Compound 2 in Combination with Induction Therapy and Consolidation Therapy in Patients with Newly Diagnosed Acute Myeloid Leukemia with an IDH1 and/or IDH2 Mutation Objectives
Primary Objective:
determine the safety and tolerability of COMPOUND 1 and (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (hereinafter COMPOUND 2) when administered with induction and consolidation therapy in patients with newly diagnosed acute myeloid leukemia (AML) with an isocitrate dehydrogenase-1 (IDH1) and/or isocitrate dehydrogenase-2 (IDH2) mutation.

Secondary Objectives:
characterize the pharmacokinetics (PK) of COMPOUND 1 and COMPOUND 2 in plasma samples when administered with AML induction therapy and consolidation therapy;

establish the recommended Phase 2 dose (RP2D) of COMPOUND 1 and COMPOUND 2 when administered with AML induction and consolidation therapy;
evaluate the 2-hydroxygluturate (2-HG) levels in plasma;
evaluate the clinical activity of COMPOUND 1 in combination with AML induction and consolidation therapy.

Study Outcome Measures
Safety Outcome Measures
Safety will be evaluated by:
dose-limiting toxicities (DLTs);
adverse events (AEs), serious adverse events (SAEs), and AEs leading to discontinuation;
safety laboratory test results, physical examination, vital signs, 12-lead electrocardiograms (ECGs), left ventricular ejection fraction (LVEF), and Eastern Cooperative Oncology Group (ECOG) performance status (PS);
drug exposure, including dose intensities and dose modifications.

Pharmacokinetic and Pharmacodynamic Outcome Measures
The PK and PD profile of COMPOUND 1 and COMPOUND 2 and will be evaluated by:
plasma concentrations and PK parameters of COMPOUND 1 and COMPOUND 2 and the major metabolite of COMPOUND 1;
plasma concentrations of 2-HG in relation to plasma concentrations of COMPOUND 1 and COMPOUND 2 over time.

Clinical Activity Outcome Measures
The clinical activity of COMPOUND 1 and COMPOUND 2 in combination with AML induction and consolidation therapy will be evaluated by:
complete remission rate (CRR);
objective response rate (ORR), including complete remission (CR), CR with incomplete hematologic recovery—neutrophil and/or platelet (CRi [includes CR with incomplete platelet recovery (CRp)]), partial remission (PR), and morphologic leukemia-free state (MLFS);
duration of response (DOR) and duration of CR (DOCR);
time to response (TTR) and time to CR (TTCR);
event-free survival (EFS);
overall survival (OS).

Study Design
COMPOUND 1 and COMPOUND 2 are administered in an open-label, multicenter, Phase 1 clinical trial to evaluate the safety of COMPOUND 1 and COMPOUND 2 in combination with AML induction and consolidation therapy. The study will evaluate 1 dose level of COMPOUND 2 in patients with an IDH1 mutation and 2 dose levels of COMPOUND 1 in patients with an IDH2 mutation. COMPOUND 1 or COMPOUND 2 will be administered with 2 types of AML induction therapies (cytarabine with either daunorubicin or idarubicin) and 2 types of AML consolidation therapies (mitoxantrone with etoposide [ME] or cytarabine). For patients who have a dual IDH1 and IDH2 mutation, assignment to COMPOUND 1 or COMPOUND 2 will be based on Investigator and Medical Monitor decision.

Patients will be treated as follows:
all patients will receive induction therapy (7+3 cytarabine, daunorubicin/idarubicin) in combination with COMPOUND 1 or COMPOUND 2;
after 1 cycle of induction therapy, patients may undergo a second induction cycle given as per institutional practice (i.e., repeat 7+3, or 7+3 at attenuated doses or schedule such as 5+2 cytarabine, daunorubicin/idarubicin). The second induction cycle may be started after the Day 14 bone marrow aspirate/biopsy (if performed) and no later than 35 days following Day 1 of the first induction;
patients who do not achieve CR or CRi (including CRp) after a maximum of 2 inductions will be discontinued from the study;
patients who achieve CR or CRi (including CRp) at the end of induction therapy will go on to receive consolidation therapy (ME or up to 4 cycles of intermediate-dose cytarabine) in combination with COMPOUND 1 or COMPOUND 2. Consolidation treatment should begin within approximately 2 weeks after hematologic recovery in the last induction cycle, or no later than 12 weeks after Day 1 of the first induction cycle;
patients who complete consolidation therapy and are in CR or CRi (including CRp) may continue on maintenance therapy and receive daily treatment with COMPOUND 1 or COMPOUND 2 for up to 1 year from Day 1 of the first induction cycle, or until relapse, development of an unacceptable toxicity, or hematopoietic stem cell transplant (HSCT) based on Investigator and Medical Monitor decision.

Response will be evaluated by the Investigator based on International Working Group (IWG) criteria.

The type of induction therapy and/or consolidation therapy each patient receives will be based on Investigator discretion and/or open cohorts.

The enrollment into each type of induction therapy will be done in parallel for the first cohort of 6 DLT evaluable patients for daunorubicin with cytarabine and idarubicin with cytarabine for COMPOUND 1 and COMPOUND 2 groups. For consolidation therapy, a minimum of 6 evaluable patients each will receive either cytarabine 1-1.5 g/m$^2$ or ME. Patients with favorable risk cytogenetics may receive 2-3 g/m$^2$ cytarabine; there is no minimum number of patients required for this group.

Definition of Dose-Limiting Toxicity
Dose-limiting toxicity is defined as any of the following AEs that are clinically significant and considered by the Investigator to be related to COMPOUND 1 or COMPOUND 2 as the single contributor or in combination with daunorubicin, idarubicin, or cytarabine.

Hematologic:
Prolonged myelosuppression, with Grade 4 neutropenia or thrombocytopenia lasting ≥42 days from Day 1 of the first induction cycle in the absence of persistent leukemia (by National Cancer Institute Common Terminology Criteria for Adverse Events [NCI CTCAE], version 4.03, leukemia-specific criteria, i.e., marrow cellularity <5% on Day 28 or later from the start of study drug without evidence of leukemia). Leukemia-specific grading should be used for cytopenias (based on percentage decrease from baseline: 50 to 75%=Grade 3, >75%=Grade 4).

Non Hematologic:
All toxicity ≥Grade 3 not due to underlying AML or complications of the disease or myelosuppressive treatment, with the exception of ≥Grade 3 blood bilirubin increases in subjects with a UGT1A1 mutation receiving COMPOUND 1. Since isolated blood bilirubin increases have been seen in subjects with a UGT1A1 mutation receiving COMPOUND 1, blood bilirubin increases of >5×upper limit of normal (ULN) may be considered a DLT in these subjects.

The definition of a DLT does not include the expected systemic and infectious complications of treatment with anthracyclines and cytarabine, including, but not limited to:
anorexia requiring total parenteral nutrition;
fatigue necessitating bed rest;

gastrointestinal infectious complications such as colitis, typhilitis, mucositis, stomatitis;

liver function test (LFT) elevations, metabolic or electrolyte laboratory abnormality that return to baseline within 14 days.

The Clinical Study Team, including representatives from the Sponsor, Medical Monitor, and participating Investigators, also will review any emergent toxicity that is not explicitly defined by the DLT criteria to determine if any warrant a DLT designation.

Toxicity severity will be graded according to the NCI CTCAE version 4.03. All AEs that cannot clearly be determined to be unrelated to COMPOUND 1 or COMPOUND 2 will be considered relevant to determining DLTs and will be reviewed by the Clinical Study Team.

DLT-Evaluable Patients

DLT-evaluable patients for induction therapy are defined as those patients who receive all doses of the first cycle of induction chemotherapy and at least 75% of COMPOUND 1 or COMPOUND 2 doses in the first 28 days from first dose of induction therapy, or experience a DLT during the first 28 days. In addition, patients must take all 3 COMPOUND 1 or COMPOUND 2 doses on Days 1 to 3 and at least 2 COMPOUND 1 or COMPOUND 2 doses on Days 4 to 7 of first induction to be considered DLT-evaluable. A patient diary will be used during outpatient treatment to record details around COMPOUND 1 and COMPOUND 2 dosing.

Safety Evaluation for Induction Therapy

This study will use a "6+6" design for COMPOUND 1 and COMPOUND 2 dose determination, which is similar to the standard "3+3" design but with more accuracy of identifying the RP2D as more patients are evaluated at each dose level. Each dose cohort will plan to enroll 6 DLT-evaluable patients, starting with Dose Level 1. Dose escalation or de-escalation decisions will be made independently for each type of induction combination therapy (i.e., cytarabine with either daunorubicin or idarubicin. For COMPOUND 2, there is only 1 dose de-escalation allowed to dose Level −1. For COMPOUND 1, there is 1 dose escalation allowed to Dose Level 2 and 1 dose de-escalation allowed to Dose Level −1.

Guidelines for Compound 1 Dose Evaluation:

If 0 or 1 of 6 patients experiences a DLT at the current dose level, that dose will be declared safe for that induction regimen. If at Dose Level 1, dose escalation will proceed to Level 2 if Level 1 is determined also to be safe in consolidation (see below). Approximately 6 additional patients will then be enrolled at Dose Level 1 as needed for evaluation of consolidation at this dose and further evaluation of safety.

If 2 of 6 patients experience a DLT, the cohort will be expanded with 6 additional patients for a total of 12 patients at this dose level.

If 3 or fewer of 12 patients experience a DLT, the current dose level will be declared safe for induction. If at Dose Level 1, dose escalation will proceed to Level 2 if Level 1 is determined also to be safe in consolidation.

If 4 or more of 12 patients experience a DLT at Dose Level 1: Dose de-escalation will proceed to Dose Level −1. If 4 or more of 12 patients experience a DLT at Dose Level 2: Return to Dose Level 1. If 4 or more of 12 patients experience a DLT at Dose Level −1: That induction regimen will be closed to further enrollment.

If 3 or more of 6 patients experience a DLT at Dose Level 1: Dose de-escalation will proceed to Dose Level −1. If 3 or more of 6 patients experience a DLT at Dose Level 2: Return to Dose Level 1. If 3 or more of 6 patients experience a DLT at Dose Level −1: hat induction regimen will be closed to further enrollment.

Guidelines for Compound 2 Dose Evaluation:

No dose escalation for Compound 2.

If 0 or 1 of 6 patients experiences a DLT at Dose Level 1, that dose level will be declared safe for that induction regimen. Approximately 6 additional patients will be enrolled at this dose level as needed for evaluation of consolidation at this dose and further evaluation of safety.

If 2 of 6 patients experience a DLT at Dose Level 1, the cohort will be expanded with 6 additional patients for a total of 12 patients at this dose level.

If 3 or fewer of 12 patients experience a DLT, Dose Level 1 will be declared safe for induction.

If 4 or more of 12 patients experience a DLT, dose de-escalation will proceed to Dose Level −1.

If 3 or more of 6 patients experience a DLT, dose de-escalation will proceed to Dose Level −1.

If the dose is de-escalated to Dose Level −1, the evaluation of that dose will occur as described above. If 3 or more of 6 patients experience or 4 or more of 12 patientsexperience a DLT at Dose Level −1, that inducrion regimen will be closed to further enrollment.

Safety Evaluation for Consolidation Therapy

The safety of consolidation therapy at each dose level will be reviewed regularly and evaluated when 6 patients have completed at least 28 days of consolidation treatment or have discontinued due to toxicity. All available safety data will be evaluated to determine if the dose is safe and tolerable.

For COMPOUND 1, the dose escalation to 200 mg requires that 100 mg is determined safe for both induction (either daunorubicin with cytarabine or idarubicin with cytarabine) and consolidation (either cytarabine 1-1.5 g/m$^2$ or ME). The daunorubicin+cytarabine+COMPOUND 1 200 mg induction cohort will open if daunorubicin+cytarabine+COMPOUND 1 100 mg is deemed safe and the idarubicin+cytarabine+COMPOUND 1 200 mg induction cohort will open if idarubicin+cytarabine+COMPOUND 1 100 mg is deemed safe. The cytarabine 1-1.5 g/m$^2$ (and cytarabine 2-3 g/m$^2$)+COMPOUND 1 200 mg consolidation cohort will open if cytarabine 1-1.5 g/m$^2$ (or cytarabine 2-3 g/m$^2$)+COMPOUND 1 100 mg is deemed safe and the ME+COMPOUND 1 200 mg consolidation cohort will open if ME+COMPOUND 1 100 mg is deemed safe.

Interim Safety Review

Interim safety reviews will be conducted following completion of each induction dosing cohort (i.e., all cohort patients have completed their DLT windows) and when the first 6 evaluable consolidation patients have completed at least 28 days of treatment or have discontinued due to toxicity.

Safety assessments include the following:

observed toxicity including DLTs;

review of AEs/SAEs;

PK/PD data;

review of cardiac and laboratory data;

bone marrow aspirate/biopsy.

The safety assessment will be made by the Clinical Study Team. Dose reduction of COMPOUND 1 or COMPOUND 2 may be made earlier for patient safety or at the discretion of the Investigator in discussion with the Sponsor.

Study Drug

A single dose of COMPOUND 1 or COMPOUND 2 will be administered orally starting on Day 1 of induction prior to daunorubicin/idarubicin and cytarabine and will be administered daily through treatment discontinuation or end of study. Doses of COMPOUND 1 or COMPOUND 2 must be taken within ±4 hours of the scheduled dose at approximately the same time each day. Each COMPOUND 1 daily dose should be taken 2 hours after fasting (water is allowed), and food intake should be avoided for at least 1 hour after administration of COMPOUND 1. All patients are advised to avoid grapefruit and grapefruit products.

The dose of COMPOUND 2 administered to patients with an IDH1 mutation will be 500 mg (unless there is a dose reduction to 250 mg due to DLTs. The dose of COMPOUND 1 administered to patients with an IDH2 mutation will be dependent upon which dose cohort is open for enrollment when the patient qualifies for the study. Dose levels are provided in 7. No intra-patient dose escalation will be permitted during induction or consolidation therapy for COMPOUND 1.

Patients who continue onto maintenance therapy following consolidation may receive daily COMPOUND 1 or COMPOUND 2 for up to 1 year from Day 1 of the first induction cycle. Patients receiving COMPOUND 2 will continue on treatment at their current dose. Patients receiving COMPOUND 1 100 mg may continue on treatment at their current dose or may have a dose escalation to 200 mg if that dose has been established as safe in induction and consolidation. Intra-patient dose escalation to 200 mg during maintenance with COMPOUND 1 should be confirmed with the Medical Monitor.

Alternative dosing schedules for COMPOUND 1 or COMPOUND 2, including administration of the same total daily dose using different schedules in concurrent cohorts, may be explored as agreed upon by the Clinical Study Team.

TABLE 7

Dose Levels for COMPOUND 1
COMPOUND 1 (IDH2 Mutation)

| Dose Level | Dose |
| --- | --- |
| −1 | 50 mg |
| 1 | 100 mg |
| 2 | 200 mg |

TABLE 8

Dose Levels for COMPOUND 2
COMPOUND 2 (IDH1 Mutation)

| Dose Level | Dose |
| --- | --- |
| −1 | 250 mg |
| 1 | 500 mg |

TABLE 9

Induction Schedule with COMPOUND 1 or COMPOUND 2

| Treatment | Day 1 | Day 2 | Day 3 | Days 4-7 | Days 8-28[a,b] |
| --- | --- | --- | --- | --- | --- |
| IV Cytarabine 200 mg/m$^2$[c] | X | X | X | X | |
| IV Daunorubicin 60 mg/m$^2$; or IV Idarubicin 12 mg/m$^2$[c] | X | X | X | | |
| Oral COMPOUND 1 or COMPOUND 2 | X | X | X | X | X |

[a]Patients may undergo a second induction cycle as per institutional practice (i.e. repeat 7 + 3, or 7 + 3 at attenuated doses or schedule such as 5 + 2 cytarabine, daunorubicin/idarubicin) starting after the Day 14 bone marrow aspirate/biopsy (if performed) and no later than 35 days following Day 1 of the first induction.
[b]Patients should take COMPOUND 1 or COMPOUND 2 on all days of the induction cycle(s) (i.e., through last day of cycle if induction cycle is longer than 28 days).
[c]Dose adjustments may be made to cytarabine, daunorubicin, and/or idarubicin as indicated by the prescribing information.

TABLE 10

Consolidation Schedule with COMPOUND 1 or COMPOUND 2

| Treatment | Day 1 | Day 2 | Day 3 | Day 4 | Day 5 | Days 6-28[a] |
| --- | --- | --- | --- | --- | --- | --- |
| IV Cytarabine[b]; or Mitoxantrone 10 mg/m$^2$ and Etoposide 100 mg/m$^2$[c,d] | X | X | X | X | X | |
| Oral COMPOUND 1 or COMPOUND 2 | X | X | X | X | X | X |

[a]A window of 28 to 42 days is allowed for each consolidation cycle. Patients should take Compound 1 or Compound 2 on all days of the consolidation cycle(s) (i.e., through last day of cycle if consolidation cycle is longer than 28 days).
[b]Cytarabine will be given at or between doses of 1 g/m$^2$ and 1.5 g/m$^2$ IV q12h, Days 1-3. Patients with favorable risk cytogenetics can receive higher doses of cytarabine at or between doses of 2-3 g/m$^2$ IV q12h, Days 1-3 or Days 1, 3, and 5. Patients may receive up to 4 consolidation cycles with cytarabine.
[c]Mitoxantrone 10 mg/m2 and Etoposide 100 mg/m2 may be chosen as consolidation regimen as per institutional practice.
[d]Dose adjustments may be made to cytarabine, mitoxantrone and/or etoposide as indicated by the prescribing information.

Estimated Number of Patients

A total of approximately 72 DLT evaluable patients (approximately 12 patients required at each dose level of COMPOUND 1 or COMPOUND 2 per each type of 7+3 induction therapy) will be enrolled in this study. Taking into account an up to 20% drop out during the DLT evaluation period, this study will enroll up to a total of approximately 90 patients. Additional patients may be enrolled in a dose level to replace patients who are not evaluable for DLT, fill consolidation cohorts, or for further exploring safety, PK, PK/PD, or preliminary clinical activity.

Inclusion Criteria

Patients are eligible for inclusion in the study if they meet the following criteria: ≥18 years of age;

previously untreated AML (de novo or secondary) defined according to WHO criteria, excluding APL [AML with t(15; 17)], with locally documented IDH1 and/or IDH2 gene mutation scheduled for induction therapy followed by consolidation therapy. Secondary AML is defined as AML arising after myelodysplastic syndromes (MDS) or antecedent hematologic disorder (AHD) or AML arising after exposure to genotoxic injury including radiation and/or chemotherapy. Patients may have had previous treatment with hypomethylating agents (HMAs) for MDS;

ECOG PS of 0 to 2;

Adequate hepatic function as evidenced by:

serum total bilirubin ≤1.5×ULN unless considered due to Gilbert's disease, a gene mutation in UGT1A1 (only for patients who will be receiving COMPOUND 1), or leukemic involvement following approval by the Medical Monitor;

aspartate aminotransferase (AST), alanine aminotransferase (ALT), and alkaline phosphatase (ALP)≤3.0×ULN, unless considered due to leukemic involvement following approval by the Medical Monitor;

adequate renal function as evidenced by serum creatinine ≤2.0×ULN or creatinine clearance >40 mL/min based on the Cockroft-Gault glomerular filtration rate (GFR);

agree to serial blood and bone marrow sampling;

meet any criteria necessary for the safe and proper use of the induction and consolidation agents involved in this trial;

able to understand and willing to sign an informed consent form. A legally authorized representative may consent on behalf of a subject who is otherwise unable to provide informed consent, if acceptable to, and approved by, the site's Institutional Review Board (IRB)/Independent Ethics Committee (IEC);

female subjects with reproductive potential must agree to undergo a medically supervised pregnancy test prior to starting study drug. The first pregnancy test will be performed at screening (within 7 days prior to first study drug administration). A pregnancy test should also be performed on the day of the first study drug administration and confirmed negative prior to dosing as well as before dosing on Day 1 of all subsequent cycles;

female subjects with reproductive potential must have a negative serum pregnancy test within 7 days prior to the start of the therapy. Subjects with reproductive potential are defined as sexually mature women who have not undergone a hysterectomy, bilateral oophorectomy or tubal occlusion or who have not been naturally postmenopausal for at least 24 consecutive months. Females of reproductive potential as well as fertile men and their partners who are female of reproductive potential must agree to abstain from sexual intercourse or to use two highly effective forms of contraception from the time of giving informed consent, during the study, and for 90 days (females and males) following the last dose of COMPOUND 1 or COMPOUND 2. A highly effective form of contraception is defined as hormonal oral contraceptives, injectables, patches, intrauterine devices, double-barrier method (e.g., synthetic condoms, diaphragm or cervical cap with spermicidal foam, cream, or gel) or male partner sterilization.

Exclusion Criteria

Patients are excluded from the study if they meet any of the following criteria:

prior chemotherapy for AML. Hydroxyurea is allowed for the control of peripheral leukemic blasts in subjects with leukocytosis (white blood cell [WBC] counts >30,000/04;

taking medications with narrow therapeutic windows, unless they can be transferred to other medications prior to enrolling or unless the medications can be properly monitored during the study;

taking known strong cytochrome P450 (CYP) 3A4 inducers or inhibitors;

taking P-glycoprotein (P-gp) or breast cancer resistance protein (BCRP) transporter-sensitive substrate medications unless they can be transferred to other medications within ≥5 half-lives prior to administration of COMPOUND 1 or COMPOUND 2, or unless the medications can be properly monitored during the study;

pregnant or breast feeding;

uncontrolled active infection or uncontrolled invasive fungal infection (positive blood or tissue culture). An infection controlled with an approved or closely monitored antibiotic/antifungal treatment is allowed;

Prior history of malignancy, other than MDS or AML, unless the subject has been free of the disease for ≥1 year prior to the start of study treatment. However, subjects with the following history/concurrent conditions are allowed:

basal or squamous cell carcinoma of the skin;

carcinoma in situ of the cervix;

carcinoma in situ of the breast;

incidental histologic finding of prostate cancer;

significant active cardiac disease within 6 months prior to the start of study treatment, including New York Heart Association (NYHA) Class III or IV congestive heart failure; myocardial infarction, unstable angina and/or stroke; or LVEF <40% by echocardiogram (ECHO) or multi-gated acquisition (MUGA) scan obtained within 28 days prior to the start of study treatment;

QTc interval using Fridericia's formula (QTcF) ≥450 msec or other factors that increase the risk of QT prolongation or arrhythmic events (e.g., heart failure, hypokalemia, family history of long QT interval syndrome). Bundle branch block and prolonged QTc interval are permitted with approval of the Medical Monitor;

taking medications that are known to prolong the QT interval unless they can be transferred to other medications within ≥5 half-lives prior to dosing (If equivalent medication is not available QTc will be closely monitored);

known infection with human immunodeficiency virus (HIV) or active hepatitis B or C;

dysphagia, short-gut syndrome, gastroparesis, or other conditions that limit the ingestion or gastrointestinal absorption of orally administered drugs;

clinical symptoms suggestive of active central nervous system (CNS) leukemia or known CNS leukemia. Evaluation of cerebrospinal fluid (CSF) during screening is only required if there is a clinical suspicion of CNS involvement by leukemia during screening;

immediate life-threatening, severe complications of leukemia such as uncontrolled bleeding, pneumonia with hypoxia or shock, and/or disseminated intravascular coagulation any other medical or psychological condition deemed by the Investigator to be likely to interfere with a patient's ability to give informed consent or participate in the study.

Duration of Treatment and End of Study

Duration of Treatment

Daily treatment with COMPOUND 1 or COMPOUND 2 will begin on the first day of induction therapy. All patients will receive 1 cycle of induction therapy. A second cycle of induction is permitted for patients according to the Investigator's discretion. After induction therapy, patients who achieve CR or CRi (including CRp) will receive consolidation therapy.

Patients achieving a CR or CRi (including CRp) who receive both induction and consolidation therapy, may continue to receive single agent COMPOUND 1 or COMPOUND 2 after consolidation therapy until relapse, development of an unacceptable toxicity, or HSCT, for up to 1 year from Day 1 of the first induction cycle.

HSCT

Subjects who achieve an adequate response and are eligible to have HSCT may proceed to HSCT after discontinuation of COMPOUND 1 or COMPOUND 2. Patients who have HSCT will be discontinued from the study and will be followed for survival.

Survival Follow-Up

After patients discontinue study treatment, they will be contacted approximately every 3 months to collect survival data for up to 1 year from the time of last patient enrolled.

End of Study

End of study (last patient last visit) is defined as the time at which all patients have either completed the 1-year survival follow-up or have died, discontinued the study, are lost to follow up, or withdrew consent prior completing the 1-year follow-up period.

Statistical Methods

Statistical analyses will be primarily descriptive. Study data will be summarized for disposition, demographic and baseline characteristics, safety, PK, PD, and clinical activity parameters. Categorical data will be summarized by frequency distributions (number and percentages of patients) and continuous data will be summarized by descriptive statistics (mean, standard deviation, median, minimum, and maximum). All data will be presented in by-patient listings. All summaries, listings, figures, and analyses will be performed by dose level/schedule.

The study data will be analyzed and reported in the primary clinical study report (CSR) based on all patients' data up to the time when all patients have completed induction therapy and consolidation therapy, if applicable, or discontinued the study treatment. Any additional data for patients continuing to receive study treatment or in follow up for survival past the data cutoff date for the primary CSR will be reported once all patients have discontinued the study.

Safety will be evaluated by the incidence of AEs, severity and type of AEs, and by the patient's vital signs, ECOG performance scores, clinical laboratory results, ECG, and LVEF data, drug exposure and modifications. Safety will be summarized using descriptive statistics by dose level/schedule and total.

Descriptive statistics will be used to summarize PK parameters for each dose level and, where appropriate, for the entire population. The relationships between dose and both maximum concentration ($C_{max}$) and area under the concentration time curve (AUC) will be explored graphically for dose-proportionality.

Descriptive statistics will be used to summarize PD parameters of 2-HG inhibition for each dose cohort and, where appropriate, for the entire population. The PK/PD relationship of COMPOUND 1 or COMPOUND 2 and 2-HG inhibition will be evaluated.

Response to treatment will be assessed by the site Investigators using the IWG criteria for AML. Objective response is defined as including all responses of CR, CRi (includes CRp), PR, and MLFS. Responses at each time point and best response will be listed by patient; best overall response rate and ORR will be summarized and two-sided 95% confidence intervals (CIs) on the response rates will be calculated. Time to response/remission will also be listed and summarized if appropriate.

Time-to-event outcomes, including DOR, EFS, and OS will be assessed using Kaplan-Meier methods, if appropriate. Median, 3-month, 6-month, and 1-year estimates with associated 95% CIs will be produced if appropriate.

In certain embodiments, AML patients treated with COMPOUND 1 and AML induction and consolidation therapy, for example undergoing the clinical protocol provided herein, will show a treatment response. In some embodiments, the treatment response is a Complete Response (CR), a Morphologic Leukemia-free State (MLFS), a Morphologic Complete Remission with Incomplete Neutrophil Recovery (CRi), Morphologic Complete Remission with Incomplete Platelet Recovery (CRp), or a Partial Remission (PR), according to modified IWG AML response criteria (Cheson, et al. J Clin Oncol 2003; 21(24):4642-9).

Example 2: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol Example 2, Step 1: Preparation of 6-trifluoromethyl-pyridine-2-carboxylic acid Diethyl ether (4.32 L) and hexanes (5.40 L) were added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. was followed by dropwise addition of dimethyl amino ethanol (327.45 g, 3.67 mol) and after 10 min. dropwise addition of 2-trifluoromethyl pyridine (360 g, 2.45 mol). The reaction was stirred under $N_2$ while maintaining the temperature below −65° C. for about 2.0-2.5 hrs. The reaction mixture was poured over crushed dry ice under $N_2$, then brought to a temperature of 0 to 5° C. while stirring (approx. 1.0 to 1.5 h) followed by the addition of water (1.8 L). The reaction mixture was stirred for 5-10 mins and allowed to warm to 5-10° C. 6N HCl (900 mL) was added dropwise until the mixture reached pH 1.0 to 2.0, then the mixture was stirred for 10-20 min. at 5-10° C. The reaction mixture was diluted with ethyl acetate at 25-35° C., then washed with brine solution. The reaction was concentrated and rinsed with n-heptane and then dried to yield 6-trifluoromethyl-pyridine-2-carboxylic acid.

Example 2, Step 2: Preparation of 6-trifluoromethyl-pyridine-2-carboxylic acid methyl ester Methanol was added to the reaction vessel under nitrogen atmosphere. 6-trifluoromethyl-pyridine-2-carboxylic acid (150 g, 0.785 mol) was added and dissolved at ambient temperature. Acetyl chloride (67.78 g, 0.863 mol) was added dropwise at a temperature below 45° C. The reaction mixture was maintained at 65-70° C. for about 2-2.5 h, and then concentrated at 35-45° C. under vacuum and cooled to 25-35° C. The mixture was diluted with ethyl acetate and rinsed with saturated $NaHCO_3$ solution then rinsed with brine solution. The mixture was concentrated at 35-45° C. under vacuum and cooled to 25-35° C., then rinsed with n-heptane and concentrated at 35-45° C. under vacuum, then degassed to obtain brown solid, which was rinsed with n-heptane and stirred for 10-15 minute at 25-35° C. The suspension was cooled to −40 to −30° C. while stirring, and filtered and dried to provide 6-trifluoromethyl-pyridine-2-carboxylic acid methyl ester.

Example 2, Step 3: Preparation of 6-(6-trifluoromethyl-pyridin-2-yl)-1 H-1,3,5-triazine-2,4-dione 1 L absolute ethanol was charged to the reaction vessel under $N_2$ atmosphere and sodium metal (11.2 g, 0.488 mol) was added in portions under $N_2$ atmosphere at below 50° C. The reaction was stirred for 5-10 minutes, then heated to 50-55° C. Dried Biuret (12.5 g, 0.122 mol) was added to the reaction vessel under $N_2$ atmosphere at 50-55° C. temperature, and stirred for 10-15 minutes. While maintaining 50-55° C. 6-trifluoromethyl-pyridine-2-carboxylic acid methyl ester (50.0 g, 0.244 mol) was added. The reaction mixture was heated to reflux (75-80° C.) and maintained for 1.5-2 hours, then cooled to 35-40° C., and concentrated at 45-50° C. under vacuum. Water was added and the mixture was concentrated under vacuum then cooled to 35-40° C., more water was added and the mixture was cooled to 0-5° C. pH was adjusted to 7-8 by slow addition of 6N HCl, a solid precipitated which was centrifuged and rinsed with water and centrifuged again. The off white to light brown solid of 6-(6-trifluoromethyl-pyridin-2-yl)-1H-1,3,5-triazine-2,4-dione was dried under vacuum for 8 to 10 hrs at 50° C. to 60° C. under 600 mm/Hg pressure to provide 6-(6-trifluoromethyl-pyridin-2-yl)-1H-1,3,5-triazine-2,4-dione.

Example 2, Step 4: Preparation of 2, 4-dichloro-6-(6-trifluoromethyl-pyridin-2-yl)-1, 3, 5-triazine POCl$_3$ (175.0 mL) is charged into the reaction vessel at 20-35° C., and 6-(6-trifluoromethyl-pyridin-2-yl)-1H-1,3,5-triazine-2,4-dione (35.0 g, 0.1355 mol) was added in portions at below 50° C. The reaction mixture was de-gassed 5-20 minutes by purging with N$_2$ gas. Phosphorous pentachloride (112.86 g, 0.542 mol) was added while stirring at below 50° C., the resulting slurry was heated to reflux (105-110° C.) and maintained for 3-4 h. The reaction mixture was cooled to 50-55° C., concentrated at below 55° C. then cooled to 20-30° C. The reaction mixture was rinsed with ethyl acetate and the ethyl acetate layer was slowly added to cold water (temperature ~5° C.) while stirring and maintaining the temperature below 10° C. The mixture was stirred 3-5 minutes at a temperature between 10 to 20° C. and the ethyl acetate layer was collected. The reaction mixture was rinsed with sodium bicarbonate solution and dried over anhydrous sodium sulphate. The material was dried 2-3 h under vacuum at below 45° C. to provide 2, 4-dichloro-6-(6-trifluoromethyl-pyridin-2-yl)-1, 3, 5-triazine.

Example 2, Step 5: Preparation of 4-chloro-6-(6-(trifluoromethyl)pyridin-2-yl)-N-(2-(trifluoromethyl)-pyridin-4-yl)-1,3,5-triazin-2-amine A mixture of THF (135 mL) and 2,4-dichloro-6-(6-trifluoromethyl-pyridin-2-yl)-1, 3, 5-triazine (27.0 g, 0.0915 mol) were added to the reaction vessel at 20-35° C., then 4-amino-2-(trifluoromethyl)pyridine (16.31 g, 0.1006 mol) and sodium bicarbonate (11.52 g, 0.1372 mol) were added. The resulting slurry was heated to reflux (75-80° C.) for 20-24 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected and rinsed with 0.5 N HCl and brine solution. The organic layer was concentrated under vacuum at below 45° C., then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 2, Step 6: Preparation of 2-methyl-1-(4-(6-(trifluoromethyl)pyridin-2-yl)-6-(2-(trifluoromethyl)-pyridin-4-ylamino)-1,3,5-triazin-2-ylamino)propan-2-ol THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) were added to the reaction vessel at 20-35° C. The resulting slurry was heated to reflux (75-80° C.) for 16-20 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected. The organic layer was concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 3: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Acetone (435.0 mL) and 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (87.0 g, 0.184 mol) were added to the reaction vessel at 20-35° C. In a separate vessel, methanesulfonic acid was added over 10 minutes to cold (0-4° C.) acetone (191.4 mL) while stirring to prepare a methane sulfonic acid solution. While passing through a micron filter, the freshly prepared methanesulfonic acid solution was added dropwise to the reaction mixture. The resulting slurry was filtered using nutsche filter and washed with acetone. The filtered material was dried for 30-40 minutes using vacuum to provide 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

Example 4: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Form 3

Crystallization to Form 3 was accomplished via the following salt formation: 1) acetone (500 ml, 4.17 vol) was charged to the crystallizer, then the mixture was agitated (550 rpm) for 10 min., 2) 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (120.0 g, 253.5 mmol) was charged into crystallizer via solid charger over 45 min., 3) the solid charger was rinsed with acetone (100 ml, 0.83 vol), 4) the reaction was stirred (550 rpm) and heated to 35° C. to obtain a clear solution (in 10 min), 5) a first portion (2%) of MSA/acetone solution (0.3 mol/L, 18.1 ml, 3.8 ml/min) was added over 5 min via a piston pump, then the pump pipeline was washed with acetone (5 ml, 0.04 vol), 6) the mixture was aged at 35° C. for 10 to 15 min, while ensuring the solution remained clear, 7) 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate seed (2.4 g as generated in Example 2, 2 wt %) was added to the clear solution, 8) a second portion (49%) of MSA/acetone solution (0.3 mol/L, 444 ml, 3.7 ml/min) was added over 2 hrs, 9) the mixture was aged at 35° C. for 30 min, 10) a third portion (49%) of MSA/acetone solution (0.3 mol/L, 444 ml, 7.4 ml/min) was added over 1 hr, 11) the mixture was aged at 35° C. for 2 hr, 12) the mixture was cooled to 20° C. for 1 hr, 13) the mixture was filtered and the cake washed with acetone (240 ml twice), 17) and dried under vacuum at 30° C.; to provide Form 3 crystals.

Having thus described several aspects of several embodiments, it is to be appreciated various alterations, modifications, and improvements will readily occur to thos skilled in

The invention claimed is:

1. A method of treating a newly diagnosed acute myeloid leukemia (AML), comprising administering to a subject a therapeutically effective amount of a mutant IDH2 inhibitor and a combination of Cytarabine and Daunorubicin as an induction therapy, further comprising administering a therapeutically effective amount of a mutant IDH2 inhibitor in combination of Mitoxantrone and Etoposide as a consolidation therapy, wherein the mutant IDH2 inhibitor is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol having the following formula:

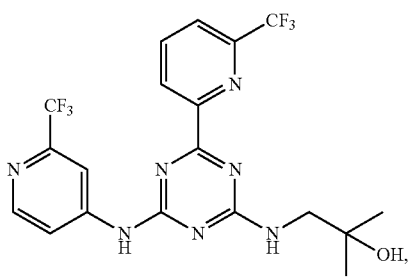 [SMILES: CC(C)(O)CNc1nc(Nc2ccnc(C(F)(F)F)c2)nc(-c2cccc(C(F)(F)F)n2)n1]

or a pharmaceutically acceptable salt, solvate, tautomer, stereoisomer, isotopologue, or a polymorph thereof (COMPOUND 1), and wherein the AML is characterized by the presence of a mutant allele of IDH2.

2. The method of claim 1, wherein between about 1 mg/m$^2$/day and about 25 mg/m$^2$/day of Mitoxantrone is administered to the subject.

3. The method of claim 2, wherein between about 5 mg/m$^2$/day and about 20 mg/m$^2$/day of Mitoxantrone is administered to the subject.

4. The method of claim 3, wherein about 10 mg/m$^2$/day of Mitoxantrone is administered to the subject.

5. The method of claim 1, wherein between about 50 mg/m$^2$/day and about 500 mg/m$^2$/day of Etoposide is administered to the subject.

6. The method of claim 5, wherein between about 75 mg/m$^2$/day and about 250 mg/m$^2$/day of Etoposide is administered to the subject.

7. The method of claim 6, wherein about 100 mg/m$^2$/day of Etoposide is administered to the subject.

8. The method of claim 1, wherein between about 100 mg/m$^2$/day and about 500 mg/m$^2$/day of Cytarabine is administered to the subject as an induction therapy.

9. The method of claim 1, wherein between about 10 mg/m$^2$/day and about 300 mg/m$^2$/day of Daunorubicin is administered to the subject.

10. A method of claim 1, wherein between about 50 mg/m$^2$/day and about 1000 mg/m$^2$/day of COMPOUND 1 is administered to the subject.

11. The method of claim 1, wherein between about 150 mg/m$^2$/day and about 300 mg/m$^2$/day of Cytarabine is administered to the subject as an induction therapy.

12. The method of claim 1, wherein about 200 mg/m$^2$/day of Cytarabine is administered to the subject as an induction therapy.

13. The method of claim 1, wherein between about 1 g/m$^2$/day and about 10 g/m$^2$/day of Cytarabine is administered to the subject as a consolidation therapy.

14. The method of claim 1, wherein between about 1 g/m$^2$/day and about 5 g/m$^2$/day of Cytarabine is administered to the subject as a consolidation therapy.

15. The method of claim 1, wherein 1 g/m$^2$/day, 1.5 g/m$^2$/day, 2 g/m$^2$/day or 3 g/m$^2$/day of Cytarabine is administered to the subject as a consolidation therapy.

16. The method of claim 1, wherein between about 30 mg/m$^2$/day and about 150 mg/m$^2$/day of Daunorubicin is administered to the subject.

17. The method of claim 1, wherein about 60 mg/m$^2$/day of Daunorubicin is administered to the subject.

18. The method of claim 1, wherein between about 150 mg/m$^2$/day and about 300 mg/m$^2$/day of COMPOUND 1 is administered to the subject.

19. The method of claim 1, wherein about 200 mg/m$^2$/day of COMPOUND 1 is administered to the subject.

20. The method of claim 1, wherein between about 50 mg/day and 1000 mg/day of COMPOUND 1 is administered to the subject.

21. The method of claim 1, wherein between about 100 mg/day and 500 mg/day of COMPOUND 1 is administered to the subject.

22. The method of claim 1, wherein is about 100 mg/day of COMPOUND 1 is administered to the subject.

* * * * *